United States Patent [19]

Faris

[11] Patent Number: 5,305,012
[45] Date of Patent: Apr. 19, 1994

[54] INTELLIGENT ELECTRO-OPTICAL SYSTEM AND METHOD FOR AUTOMATIC GLARE REDUCTION

[75] Inventor: Sadeg M. Faris, Hawthorne, N.Y.

[73] Assignee: Reveo, Inc., Hawthorne, N.Y.

[21] Appl. No.: 869,566

[22] Filed: Apr. 15, 1992

[51] Int. Cl.$^5$ ............................................. G09G 1/00
[52] U.S. Cl. .......................................... 345/7; 345/84; 359/604
[58] Field of Search .................... 340/705, 784, 980; 358/103; 359/38, 601, 630, 230; 364/449; 382/1; 345/7, 8, 9, 84, 105

[56] References Cited

U.S. PATENT DOCUMENTS

| | | | |
|---|---|---|---|
| 4,028,725 | 6/1977 | Lewis | 340/980 |
| 4,286,308 | 8/1981 | Wolff . | |
| 4,303,394 | 12/1981 | Berke et al. . | |
| 4,439,157 | 3/1984 | Breglia et al. . | |
| 4,513,317 | 4/1985 | Ruoff, Jr. . | |
| 4,568,159 | 2/1986 | Baldwin . | |
| 4,601,053 | 7/1986 | Grumet | 382/1 |
| 4,676,601 | 6/1987 | Itoh et al. | 359/38 |
| 4,679,906 | 7/1987 | Brandenburg . | |
| 4,687,072 | 8/1987 | Komuro | 340/705 |
| 4,768,028 | 8/1988 | Blackie | 340/705 |
| 4,788,594 | 11/1988 | Ovshinsky et al. . | |
| 4,799,768 | 1/1989 | Gahan . | |
| 4,818,011 | 4/1989 | Cherian . | |
| 4,828,380 | 5/1989 | Cherian . | |
| 4,843,892 | 7/1989 | Krist . | |
| 4,858,989 | 8/1989 | Bruckstein . | |
| 4,874,195 | 10/1989 | Lu et al. . | |
| 4,937,665 | 6/1990 | Schiffman | 340/705 |
| 4,943,140 | 7/1990 | Woodard et al. . | |
| 4,965,840 | 10/1990 | Subbarao . | |
| 4,973,136 | 11/1990 | Braatz | 359/38 |
| 4,984,179 | 1/1991 | Waldern | 340/980 |
| 4,986,592 | 1/1991 | Kaiser et al. . | |
| 4,994,204 | 2/1991 | Doane et al. . | |
| 4,994,794 | 2/1991 | Price et al. | 340/705 |
| 5,016,282 | 5/1991 | Tomono et al. . | |
| 5,016,970 | 5/1991 | Yoshino . | |
| 5,022,781 | 6/1991 | Smith . | |
| 5,027,200 | 6/1991 | Petrossian et al. | 358/103 |
| 5,040,877 | 8/1991 | Blinc et al. . | |
| 5,076,674 | 12/1991 | Lynam . | |
| 5,081,542 | 1/1992 | Efron et al. | 340/705 |
| 5,099,229 | 3/1992 | Aoki | 340/705 |
| 5,113,177 | 5/1992 | Cohen | 340/705 |
| 5,115,398 | 5/1992 | De Jong | 364/449 |
| 5,117,302 | 5/1992 | Lipton . | |
| 5,258,607 | 11/1993 | Agostini et al. | 259/230 |

OTHER PUBLICATIONS

"Polymer-Dispersed and Encapsulated Liquid Crystal Films" by G. Montgomery, Jr. published in Large-Area Chromogenics: Materials and Devices for Transmittance Control, SPIE Institute Series vol. IS4, pp. 577–606.

(List continued on next page.)

Primary Examiner—Alvin E. Oberley
Assistant Examiner—Steven J. Saras
Attorney, Agent, or Firm—Hopgood, Calimafde, Kalil, Blaustein, & Judlowe

[57] ABSTRACT

An electro-optical system and method are disclosed for modulating the intensity of light rays propagating towards an optical element, such as an eye, a lens or aperture stop in a camera station, a camera station in a machine vision system, or other image detection device. The electro-optical system comprises an electro-optical element having a optically transparent surface having electrically addressable pixels. Each pixel has a light transmittance which is controllable by a controller that is operably associated with a computer system. An image acquisition device, such as a camera station, acquires an image of a spatial scene within the field of view of the optical element. The computer system processes the image to determine which pixels are to be addressed and actively driven in order to modulate (i.e. decrease) the intensity of incident light rays propagating through the determined pixels, towards the optical element. Illustrated uses for the present invention include glare and spatial noise reduction in the automotive, navigational, robotic and recreational arts.

42 Claims, 22 Drawing Sheets

OTHER PUBLICATIONS

"Reverse-Mode Microdroplet Liquid Crystal Display" by Y.-D. Ma and B.-G. Wu published in Liquid Crystal Displays and Applications (1990), SPIE Institute Series vol. 1257, pp. 46-57.

"Liquid-Crystal Display Prospects in Perspective" by Allan R. Kmetz, published in IEEE Transactions on Electron Devices, vol. Ed-20, No. 11.

"Eyegaze Eyetracking System" by Dixon Cleveland and Nancy Cleveland LC Technologies, Inc., Fairfax, Va.

"The Eyegaze Development System-A Tool for Human Factors Applications" by LC Technologies, Inc., Fairfax, Va.

"The EyeGaze Computer System" by LC Technologies, Inc., Fairfax, Va. The EyeMouse by Glenn Myers, published in T.H.E. Journal, Zenith Data EyeMouse Systems, pp. 13-15.

"Electronic Interface for High-Frame-Rate Electrically Addressed Spatial Light Modulators," by S. P. Kozaitis et al., published by SPIE-The International Society for Optical Engineering, SPIE vol. 1474, pp. 112-115.

"Vision-A Computational Investigation into the Human Representation and Processing of Visual Information" by David Marr published by W. H. Freeman and Company, pp. 111-159.

"12.5: Wide-Angle-View PDLC Displays" by J. W. Doane et al., published in SID 90 Digest, pp. 224-227.

"Polymer-Dispersed Liquid Crystals: Boojums at Work" by J. William Doane.

"Application of the Phase and Amplitude Modulating Properties of LCTV's" by James C. Kirsh et al. published by Optical Technology for Signal Processing Systems (1991) SPIE vol. 1474, pp. 90-101.

"Problems of Nighttime Visibility and Glare for Older Drivers" by Paul L. Olson of SAE Technical Paper Series II 881756.

"Development of Liquid Crystal Day and Night Mirror For Automobiles" by Hideaki Ueno, et al. SAE Technical Paper Series #880053.

"Nighttime Effectiveness of Rearview Mirrors: Driver Attitudes and Behaviors" by M. Flannagan et al., SAE Technical Paper Series #900567.

"Electrochromic Materials for Automotive Applications" by H. Ahsan Habib published by SAE Technical Paper Series #910542.

"Electrically-Controlled Light Transmission Glazing For Automotive Applications Based on NCAP Technology" by Peter van Konynenburg SAE Technical Paper Series #891113.

"Corneal Lens Goggles and Visual Space Perception" by Itzhak Hadani.

"Robot Vision", The MIT Electrical Engineering and Computer Science Series by Berthold Klaus Paul Horn.

INTELLIGENT ELECTRO-OPTICAL SYSTEM AND METHOD FOR AUTOMATIC GLARE REDUCTION

FIELD OF THE INVENTION

In general, the present invention relates to a method and apparatus for selectively reducing in real-time, the intensity of incident light rays propagating towards an optical element such as an eye, a camera station in a machine vision system or other image detection device.

More particularly, the present invention relates to an intelligent electro-optic system which automatically eliminates glare produced by intense sources of illumination present in the environment.

BACKGROUND OF THE INVENTION

It is well known that intense sources of illumination can produce glare which impairs the operation of various types of optical systems.

For example, automobile drivers at night face the hazard of glare produced when intense light from the headlamps of oncoming cars impinges onto their eyes. When the headlamps of oncoming vehicles are operated in their high-beam mode, the light produced therefrom is often so intense as to disable the driver from viewing the road ahead. This problem tends to worsen as the driver's eyes are exposed to prolonged periods of headlamp illumination. Consequently, the driver's vision becomes fatigued and impairing his or her ability to drive effectively and thus presenting hazardous situations.

The above problem is particularly severe for the increasing elderly population. It is well known that older men and women tend to lose their ability to adapt to rapid changes in light intensity, making them more vulnerable to intense illumination produced from oncoming headlamps. Consequently, many older men and women avoid driving at night, depriving them the freedom to do things they once used to do.

OBJECTS OF THE INVENTION

Accordingly, it is a primary object of the present invention to provide an intelligent electro-optic system which automatically reduces the intensity of incident light rays from intense sources of illumination.

A further object of the present invention is to provide an intelligent electro-optical system which automatically modulates the intensity of light rays from propagating from points of illumination in spatial scenery to the eyes of the user viewing the spatial scenery.

A further object of the present invention is to provide an intelligent electro-optical system for reducing glare while operating an automotive vehicle, yet without impairing the driver's vision or ability to drive effectively.

Another object of the present invention is to provide an intelligent electro-optical system which automatically reduces glare when a driver views spatial scenery through either the front windshield, the rear view mirror, or the side view mirrors of an automotive vehicle.

Yet a further object of the present invention is to provide a portable electro-optical system in which a camera station is embodied in a head support frame having a pair of optically transparent electro-optical lenses, each disposed in front of one of the user's eyes to selectively filter out sources of solar and/or headlight glare.

These and further objects of the present invention will become apparent hereinafter.

SUMMARY OF THE INVENTION

In accordance with one of the broader aspects of the present invention, the method and apparatus are provided for selectively reducing the intensity of light rays as they propagate from a spatial scene towards an optical element, such as an eye or camera, having a field of view.

In general, the apparatus comprises an electro-optical element, image acquisition means, image processing means and control means. The electro-optical element has an optically transparent surface consisting of a plurality of pixels. Each pixel has a controllable light transmittance for selectively reducing the intensity of light rays propagating from a point in a spatial scene, through the pixel, then towards the optical element. The image acquisition means is provided for acquiring an image of the spatial scene within the field of view of the optical element. The image processing means is provided for processing the image and determining at which pixels the light transmittance is to be actively controlled in order to reduce the intensity of incident light rays by a selective amount before they reach the optical element. The control means is provided for actively controlling the light transmittance of the determined pixels so that as incident light rays propagate through the determined pixels, the incident light rays impinge the optical element with an intensity reduced by the selected amount.

BRIEF DESCRIPTION OF THE DRAWINGS

For a full explanation of the present invention, the following Detailed Description of the Illustrated Embodiments is to be read in conjunction with the accompanying drawings, wherein.

DETAILED DESCRIPTION OF THE ILLUSTRATIVE EMBODIMENTS

Figure 1:
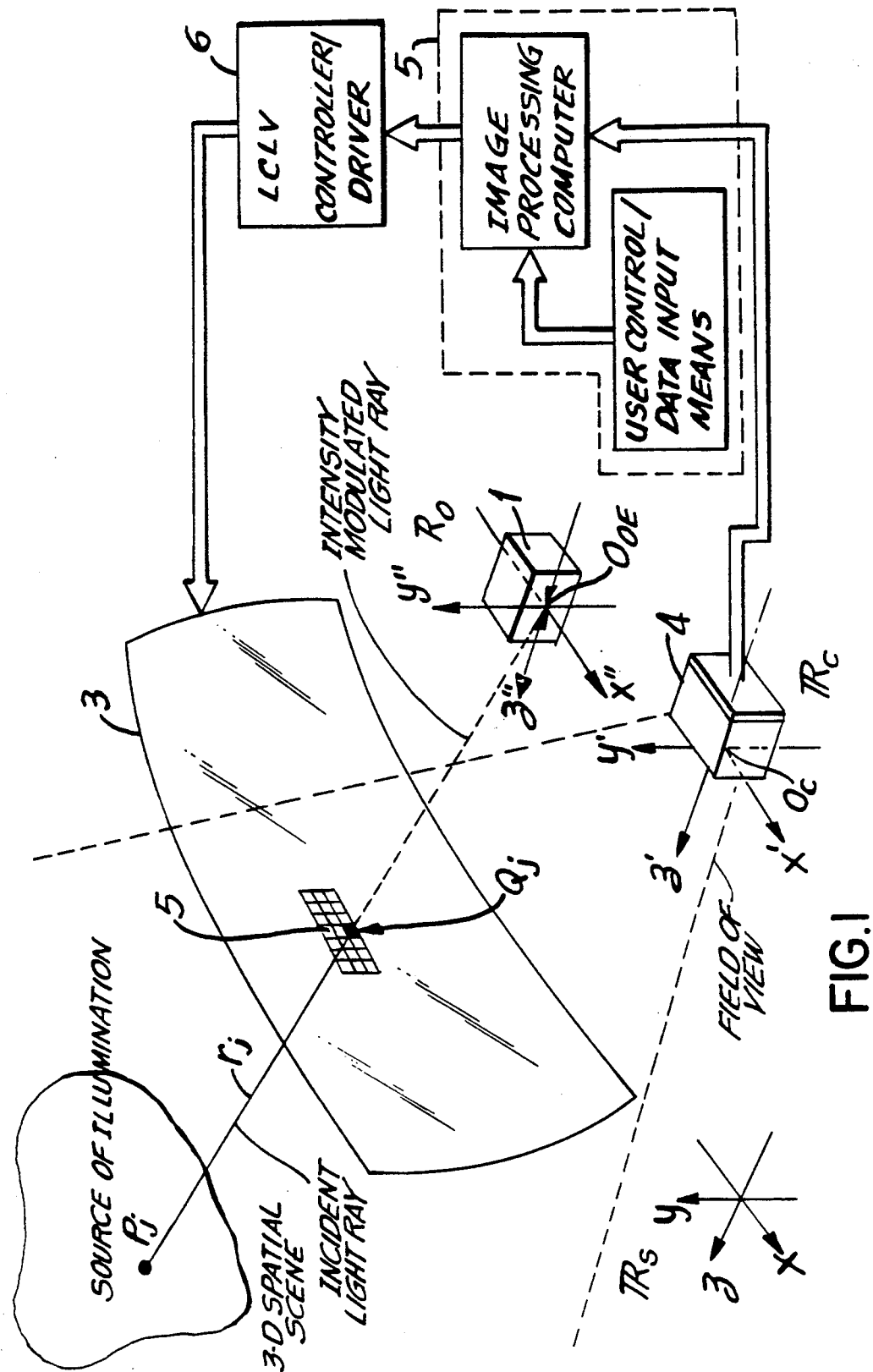
FIG. 1 is a schematic diagram illustrating a generalized electro-optical system of the present invention, in which the intensity of an incident light ray propagating from a point of illumination in a 3-D spatial scene towards an optical element, is reduced in intensity at the point of intersection through the light intensity reducing surface of the system prior to reaching the optical element.

In FIG. 1, the apparatus of the present invention is generally illustrated in the form of an intelligent electro-optical system. The primary function of electro-optical system is to selectively reduced (i.e. decrease) the intensity of incident light rays as they propagate from a three-dimensional (3-D) spatial scene towards an optical element 1. In accordance with the invention, the optical element may be the pupil of a human eye, or the aperture stop or lens of a camera station, machine vision system or any other image detection device. As illustrated, the optical element is disposed at a selected distance from the spatial scene and has a field of view in the direction thereof.

In general, the electro-optical system of the present invention comprises a number of system components, namely: an electro-optical element 3, an image acquisition means 4, an image processing means 5, and a control means 6 operably associated as shown. As illustrated, the electro-optical element has an optically transparent surface consisting of a large number of optically transparent pixels 5. Each of these pixels is electrically addressable by controller 6, and has a light transmittance which is actively controllable for the purpose of selectively reducing the intensity of an incident light ray $r_j$ propagating from a point $P_i$ in the spatial scene, through the pixel, towards the optical element. Typically, points on the surface of electro-optical element 3 are measured with respect to a coordinate system $R_s$. While the coordinate system $R_s$ is a Cartesian coordinate system specified by principal coordinate axes x, y and z, it is understood that other types of coordinates systems may be used.

Preferably, the pixels along the transparent surface are formed from a polymer-dispersed liquid crystal film having a light transmittance of at least 70% in the optical spectrum, that is, when the pixels are not actively controlled or driven by controller 6. Each pixel located on the optically transparent surface at coordinates (x, y) is electrically addressable by an address value $A(x,y)$ computed by computer system 5. When driving an addressed pixel or set of pixels at any particular instant in time, the intensity (i.e. amplitude) of incident light rays falling upon these actively driven pixels is intensity reduced by a selected amount which is sufficient to achieve effective reduction of glare produced in diverse environments. The degree of intensity reduction achievable at each pixel can be of a binary nature (i.e., a first light transmittance when not actively driven, or a lesser light transmittance when actively driven). Alternatively, the degree of intensity reduction m(x, y) can be quantized to one of a number of possible states. For further details regarding suitable polymer-dispersed liquid crystal films that may be used in practicing the present invention, reference is made to the following publications: "Reverse-Mode MicroDroplet Liquid Crystal Display" by Y. D. Ma and B. G. Wu, on pages 46–57, SPIE Vol. 1257, Liquid Crystal Displays and Application (1990); and "Polymer-Dispersed and Encapsulated Liquid Crystal Films", by G. Paul Montgomery, Jr., on pages 577–606, SPIE Institute Series Vol. IS4, Large-Area Chromogenics: Materials and Devices for Transmittance Control 1990, which are hereby incorporated by reference.

In general, image acquisition means 4 is realizable as a camera station having image forming optics and a CCD image detection array. The coordinates of pixels on the image detection array are measured with respect to coordinate system $R_c$. As illustrated, a coordinate system $R_{oe}$, specified by principal axes x', y' and z', is embedded in the optical element for measuring the position of points therein. The principal function of the camera station is to acquire images of the spatial scene within the field of view of the optical element. While not essential to the invention, these images may be acquired along the field of view of the optical element when as viewed, for example, through the optically transparent surface of electro-optical element 3, as shown in FIG. 1.

Image processing means 5 is realizable as a microcomputer system having associated memory for buffering acquired images. The microcomputer processes the acquired image(s) from the camera station in order to determine at which pixels in the electro-optical surface, the light transmittance is to be actively controlled in order to reduce the intensity of incident light rays by a selected amount before they reach the optical element. The microcomputer produces intensity reduction data m(x,y) representative of the selected amount of intensity reduction at the pixels located at coordinates x, y.

Control means 6 is realizable as controller/driver circuitry interfaced with the microcomputer 5. The principal function of control means 6 is to automatically address particular pixels and actively control the light transmittance thereof accordance with intensity reduction data m(x,y). In this way, as light rays propagate from the spatial scene and through the actively controlled pixels in electro-optical surface 3, the incident light rays propagating through these pixels will reach the optical element with an intensity that has been reduced by the selected amount of light transmittance (e.g. 30%).

Referring to FIGS. 2 through 5B, the first illustrated embodiment of the electro-optical system of the present invention will be described. In this and other embodiments illustrated hereinafter, the optical element(s) being "protected" by the electro-optical system of the invention are the eyes of an automobile driver. It is understood however, that the optical element(s) may be the camera station(s) of a machine vision system, or any image detection device desiring or requiring protection from intense sources of environmental illumination.

Figure 2:
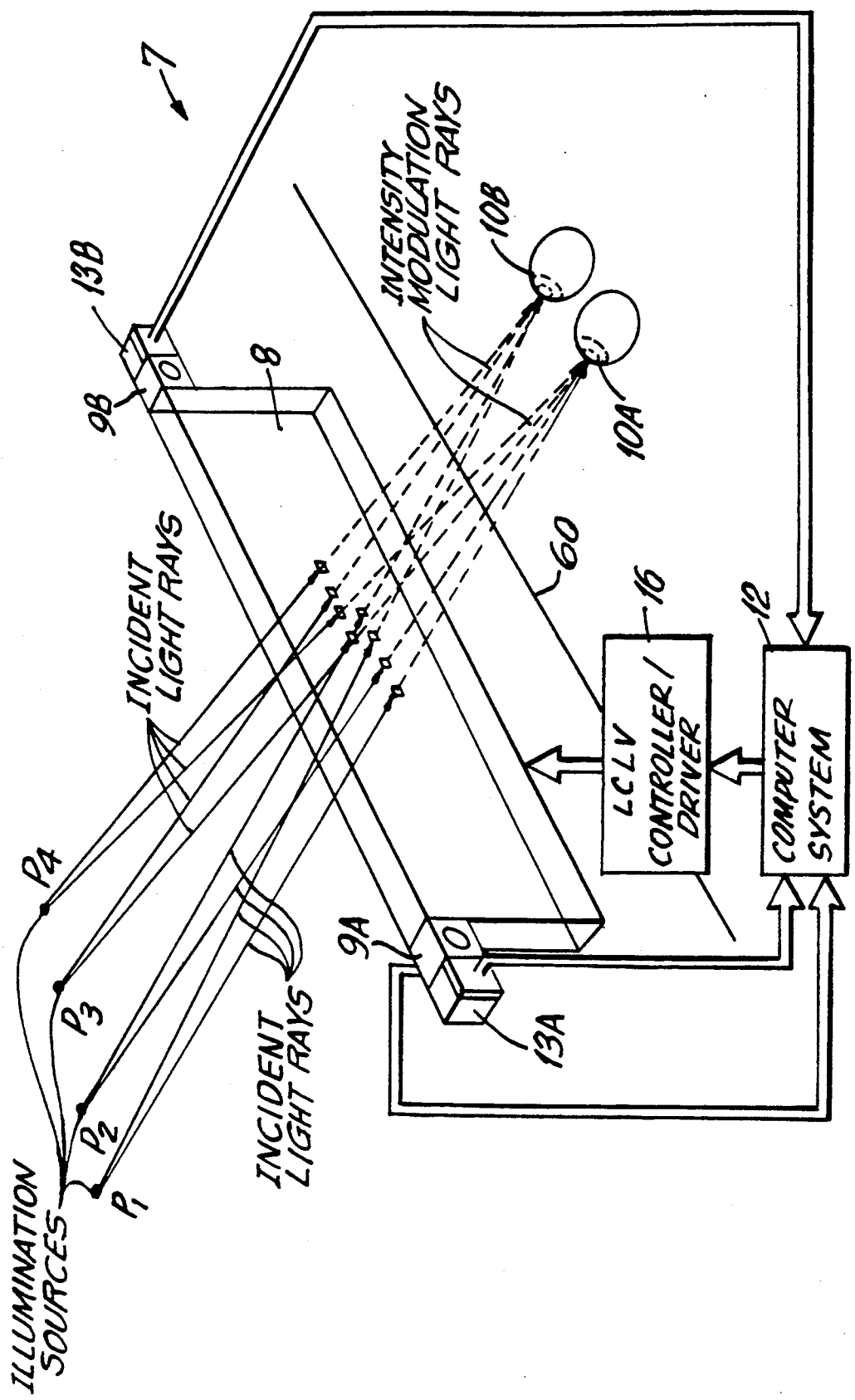
FIG. 2 is a schematic diagram illustrating the configuration of a first embodiment of the electro-optical system of the present invention, in which the light modulating surface is an optically transparent liquid crystal light valve panel carrying a stereo scene-imaging subsystem for imaging spatial scenery within the field of view of an automobile driver, and a stereo pupil-tracking camera subsystem for measuring the position of the driver's pupils relative to the liquid crystal light valve panel.

As illustrated in FIG. 2, the electro-optical element of system 7 is in the form of an optically transparent liquid crystal light valve (LCLV) panel 8 adapted for pivotal mounting inside an automobile above the dashboard in a manner similar to a conventional sunvisor. Preferably, the width of LCLV panel 8 is about 60 centimeters, the height thereof about 10 centimeters, and the size of each pixel about 2.5 millimeters, although it is well understood these dimensions will vary from embodiment to embodiment. On opposite sides of the upper portion of the LCLV panel, a pair of infrared cameras 9A and 9B are mounted with their optical axes directed towards the automobile driver in order to form a pupil-tracking camera subsystem which measures the position of the driver's pupils 10A and 10B relative to the LCLV panel. In general, each camera station comprises image forming optics and a CCD image detection array responsive to the infra-red radiation naturally emitted from the driver's eyes. Techniques for determining the position of the driver's pupils from an acquired pair of stereo infrared images, are well known in the art and are described in detail in Chapter 13, "Photogrammetry & Stereo", on pages 299–327 of Robot Vision (1991) by Berthold Klaus Paul Horn, published by MIT Press, Cambridge, Massachusetts.

Figure 4A:
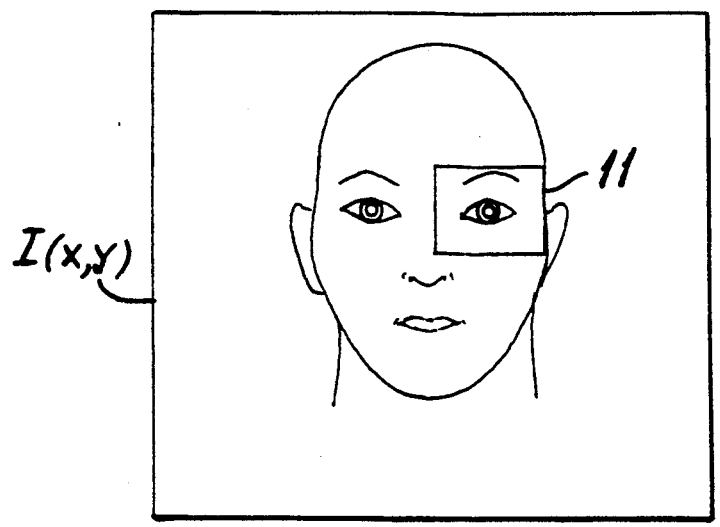
FIG. 4A is a schematic representation of an image of a driver's face produced by a camera station in the pupil-tracking camera subsystem.
Figure 4B:
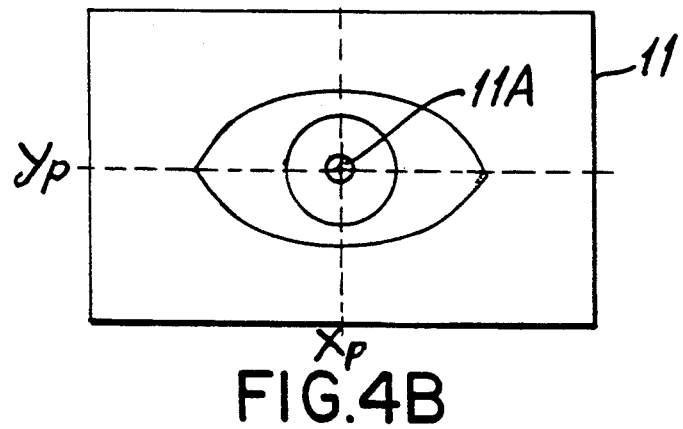
FIG. 4B is a schematic representation of an enlarged image of the driver's pupil represented in FIG. 4A.
Figure 4C:
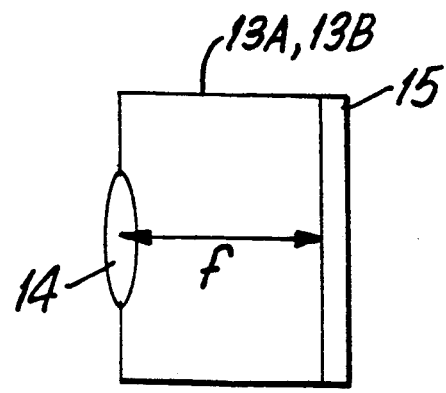
FIG. 4C is a schematic diagram of a camera station employed in the stereo camera subsystems of the electro-optical system of the present invention.

As illustrated in FIGS. 4A and 4B, the method of pupil position determination generally involves first recognizing the driver's eye 11 and then the center portion 11A of the pupil. Then pixel data at center 11A is processed by computer 12 using known stereo image processing techniques, to produce coordinate data x, y, z corresponding to the position of the pupil. This process is performed for both eyes to continuously provide coordinate data regarding the position of the driver's pupils.

On opposite sides the upper portion of the LCLV panel, adjacent infra-red cameras 9A and 9B, a pair of camera stations 13A and 13B are mounted with their optical axes directed away from the automobile driver, into the direction of oncoming traffic. Together, these camera stations form a stereo scene-imaging camera subsystem which images spatial scenery within the driver's field of view extending through the automobile windshield. As with the infra-red camera stations, Camera stations 13A and 13B include image forming optics 14 and a CCD image detection array 15, such as shown for example in FIG. 4C. On the basis of a stereo image pair acquired by the scene-imaging camera subsystem, depth-map data (i.e. x, y and z coordinates) of each point in the spatial scene can be readily computed by computer 12 using techniques discussed in detail in Chapter 13 of Robot Vision, supra. Upon processing the captured stereo images of the spatial scene and the computed pupil position data, computer 12 generates addresses A(x,y) and intensity reduction data m(x,y) corresponding to those pixels which require a change in light transmittance. This data is provided to controller/driver 16 which, in turn, addresses particular pixels coinciding with high intensity points in the spatial scene. The controller/driver then drives these addressed pixels in order to actively control the light transmittance thereof and decrease the intensity of incident light rays while propagating through actively driven pixels. As a result, the spatial scenery viewed by the automobile driver is automatically devoid of glare commonly associated with intense sources of illumination, such as the headlamps of oncoming vehicles.

Figure 3:
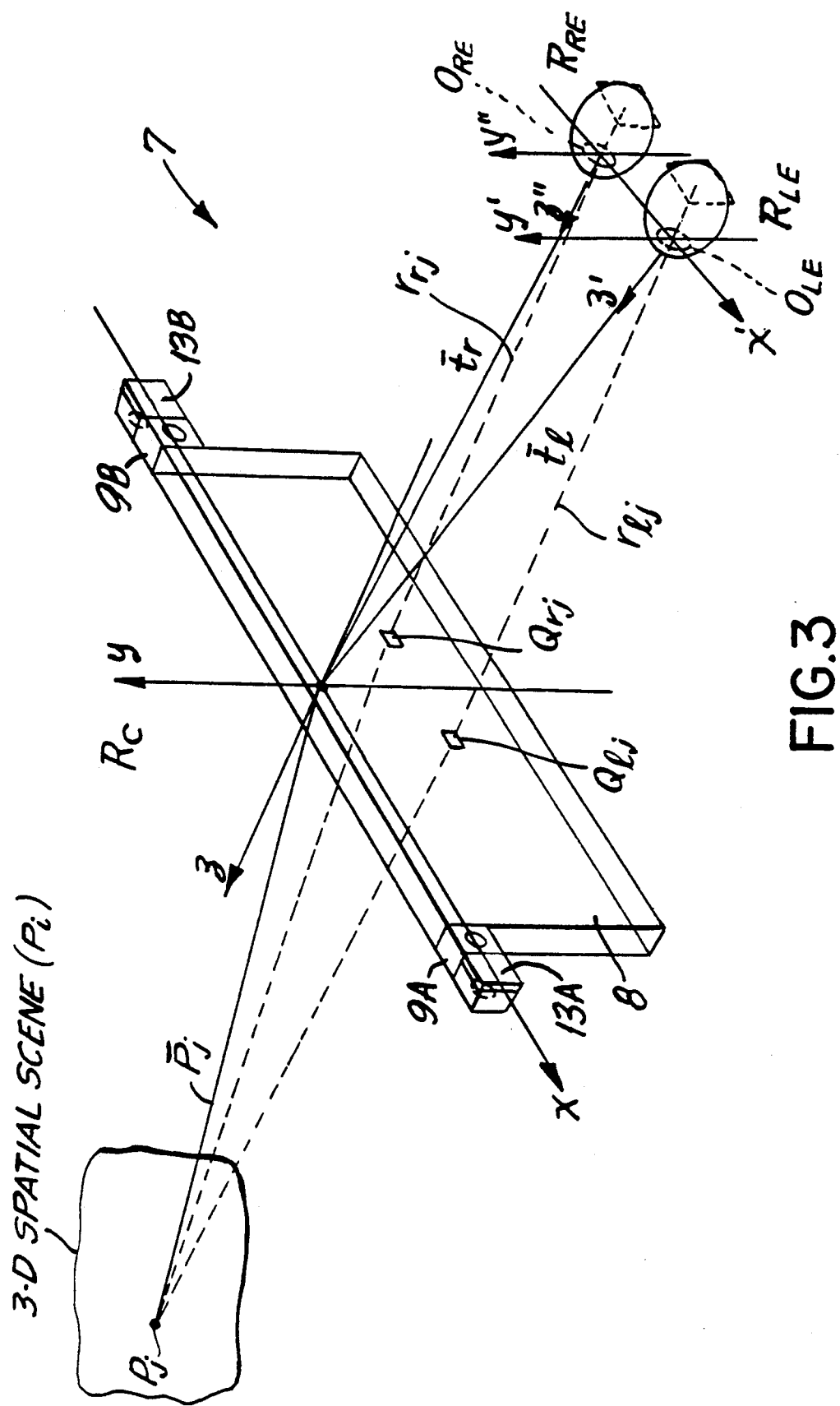
FIG. 3 is a schematic diagram illustrating the operation of the electro-optical system of FIG. 2, as light rays propagate from a point of illumination in the spatial scene, through the liquid crystal light valve panel and then intensity reduced prior to passing through the pupils of the driver's eyes.

In FIG. 3, a ray optics model is presented for the electro-optical system of FIG. 2. As shown, coordinate system $R_c$, specified by x, y and z axes, is embedded within the LCLV panel so that (i) the x-y plane lies within the planar surface of the LCLV panel, (ii) the x axis is perpendicular to the optical axes of camera stations 9A, 9B, 13A and 13B, and (iii) the z axis is parallel with the optical axes of camera stations 13A and 13B and antiparallel with camera stations 9A and 9B. Typically, the position of pixels in the CCD array of the pupil-tracking and scene-imaging camera substations are specified by coordinates measured in local coordinate systems (not shown), and can be converted to coordinate system $R_c$ using homogenous transformations well known in the art.

Disposed at the center of the pupil of the driver's left is the origin of coordinate system $R_{LE}$, which is specified by axes x', y' and z', with the z' axis aligned with the optical axis of the driver's left eye. Disposed at the center of the pupil of the driver's right eye is the origin of coordinate system $R_{RE}$, which is specified by axes x", y" and z" with the z" axis aligned with the optical axis of the driver's right eye and the y" axis aligned with the x' axis of coordinate system $R_{LE}$, as shown. The position of origin $O_{LE}$ of coordinate system $R_{LE}$, is specified by position vector $t_L$ defined in coordinate system $R_c$. Similarly, the position of the origin $O_{Re}$ of coordinate system $R_{RE}$ is specified by position vector $t_r$ defined in coordinate system $R_c$. Points $P_i$ in the scene are specified in coordinate system $R_c$ by coordinates $(x_i, y_i, z_i)$, and points in the scene having an intensity above a predetermined threshold are designed as $P_j$. The position of point $P_i$ in coordinate system $R_c$ is specified by coordinates $(x_j, y_j, z_j)$.

A light ray propagating from a point $P_j$ in the spatial scene (by a reflection or radiation process), through the transparent surface of LCLV panel 8 and then finally towards the pupil of the driver's left eye, is specified by a 3-D line equation, $r_{Lj}$. Similarly, a light ray propagating from a point $P_j$ in the spatial scene, through the LCLV panel, and then finally towards the pupil of the driver's right eye, is specified by a 3-D line equation, $r_{rj}$. The point at which light ray $r_{Lj}$ intersects the optically transparent surface of the LCLV panel is designated by $Q_{Lj}$, whereas the point at which light ray $r_{rj}$ intersects the transparent surface is designated by $Q_{rj}$.

As the driver views spatial scenery through both the LCLV panel and the automobile window, a number of steps are repeatedly performed by the intelligent electro-optical system 7, permitting the driver to operate the automobile, while light reducing (e.g. blocking) pixel locations are automatically determined, electrically addressed and actively driven on a real-time basis to reduce glare associated with oncoming headlights.

Figure 5A:
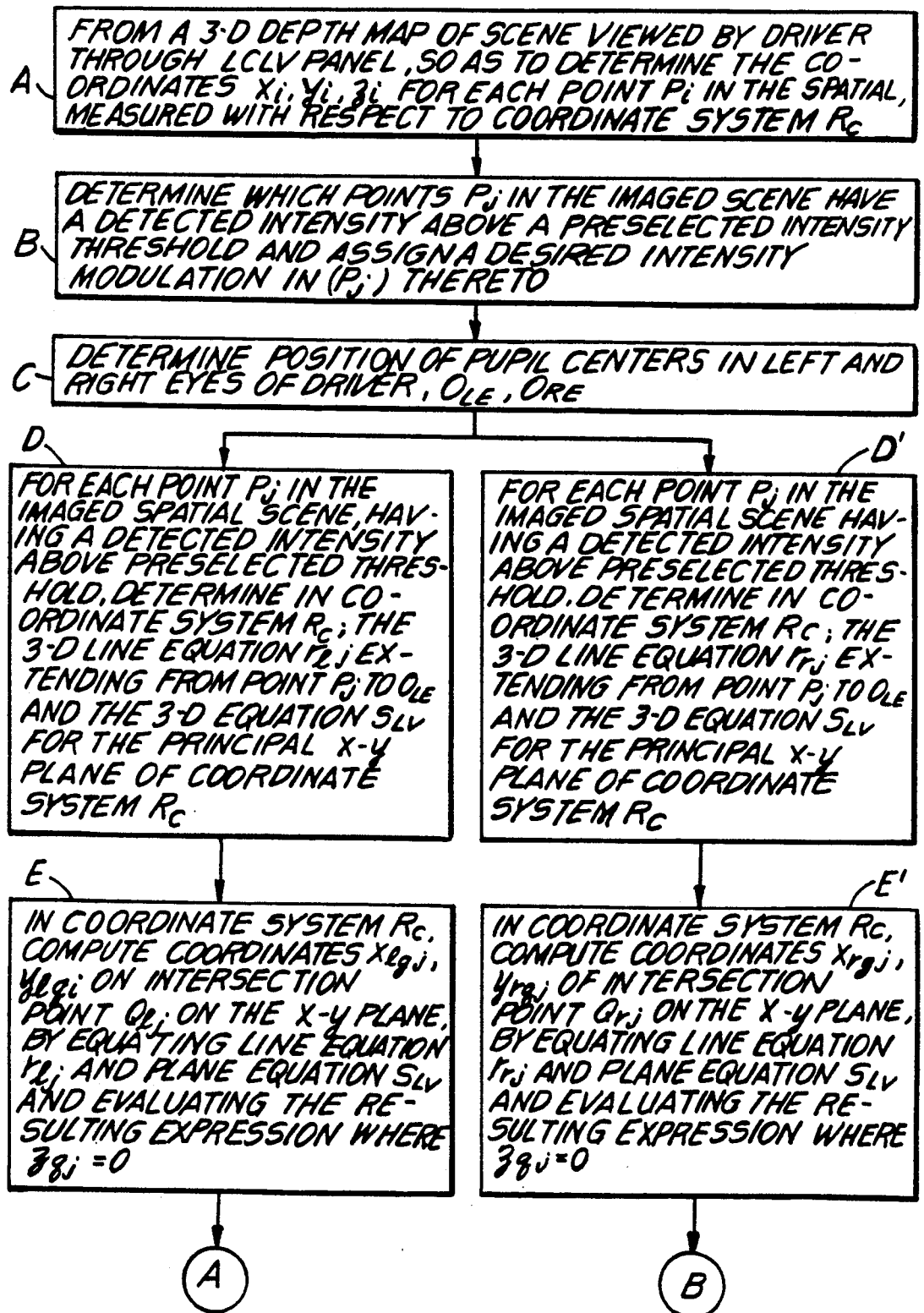
FIG. 5A and 5B is a flow chart showing the steps performed in determining the pixel locations of the liquid crystal light valve panel of the system of FIG. 2, which are electrically addressed and actively controlled in order to reduce the intensity of light rays propagating from a point of illumination in the spatial scene, towards the eyes of the driver.
Figure 5B:
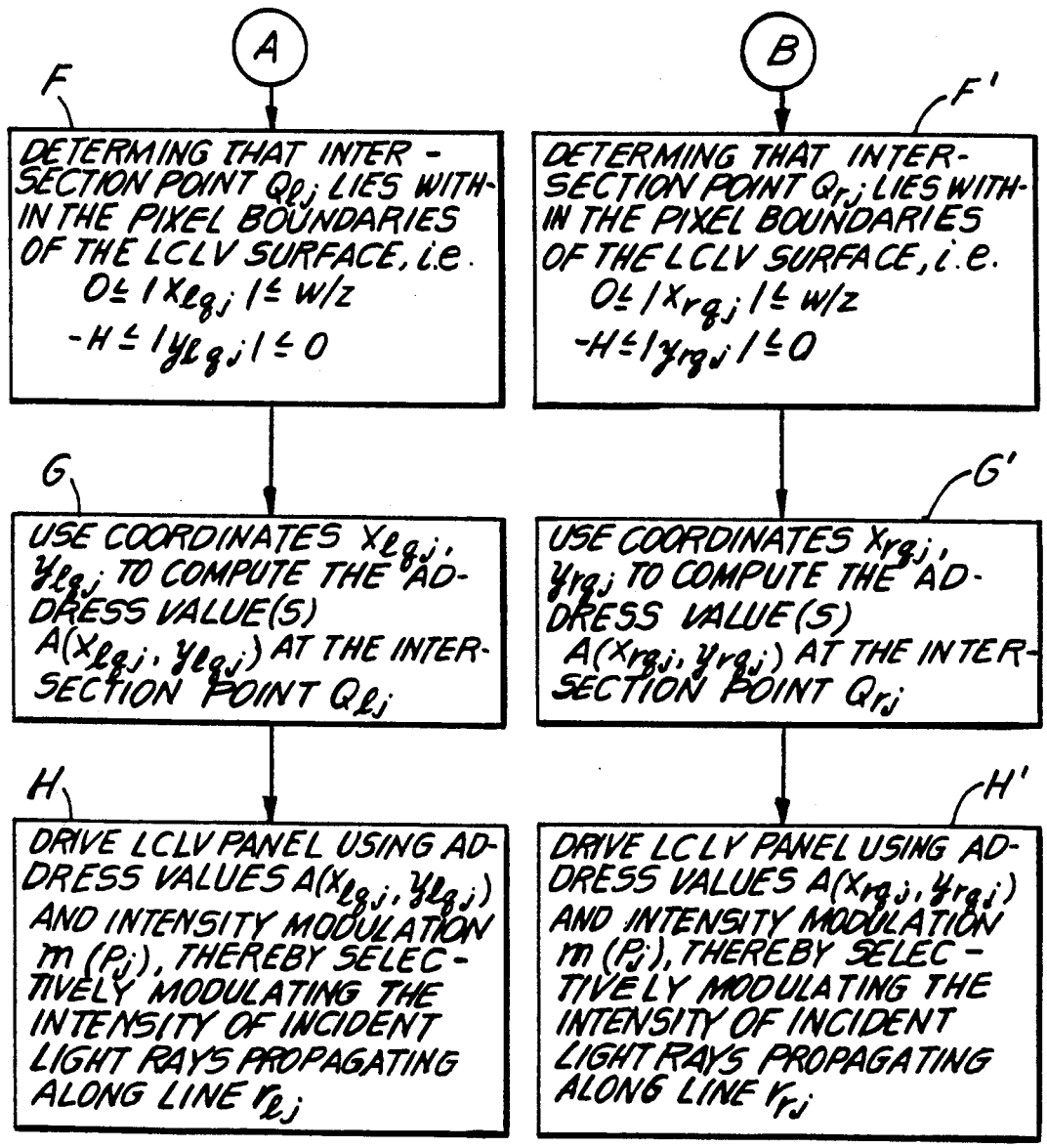

In FIGS. 5A and 5B, a generalized process is described for automatically modulating the intensity of light rays propagating through the LCLV panel of electro-optical system 7, towards the eyes of the automobile driver. As indicated at block A of FIG. 5A, the first step of the process involves forming a 3-D depth map of the spatial scene being viewed by the driver through the LCLV panel. This step results in determining the $x_i, y_i, z_i$ coordinates for each point $P_i$ in the spatial scene, measured with respect to coordinate system $R_c$. As indicated at block B, computer 12 determines which points $P_i$ in the imaged scene have a detected intensity above a preselected intensity threshold, and assigns to each of these points $P_j$, a desired intensity reduction $m(P_j)$. Then, as indicated in block C, the computer processes acquired images of the driver's eyes in order to determine the position coordinate of the pupil centers, i.e. $O_{Le}, O_{re}$, measured with respect to coordinate system $R_c$.

As indicated at blocks D through H, the computer uses the coordinates of point $P_j$ (derived from the pair of scene images) and the pupil position coordinates (derived from the pair of eye images) in order to formulate a representation of a light ray path extending from point $P_j$ in the spatial scene to the driver's left pupil. The computer then computes the pixel coordinates through which the light ray $r_{Lj}$ intersects, and then LCLV controller/driver 16 electrically addresses and actively drives each such pixel. Simultaneously, as indicated at blocks D' through H', these basis steps are performed for light rays propagating along pathways $r_{Lj}$ extending from point $P_j$ in the spatial scene to the pupil of the driver's right eye. The specifics of such subprocesses will be described below.

As indicated at block D, the computer formulates in coordinate system $R_c$ for each point $P_j$, the 3-D line equation $r_{ej}$ extending from point $P_j$ to point $O_{Le}$. The computer also formulates the 3-D surface equation $S_{LCLV}$ for the principal x-y plane of coordinate system $R_c$. As indicated at block E, the computer system then computes coordinates $x_{Lqj}, y_{Lqj}$ of the intersection point $Q_{Lj}$ on the x-y plane of coordinate system $R_c$. This can be achieved by equating 3-D line equation $r_{ej}$ and 3-D plane equation $S_{LCLV}$, and then evaluating the resulting expression where $z=0$. As indicated at block F, the computer then checks to determine whether the computed intersection point $Q_{Lj}$ lies within the light intensity reducing boundaries of the LCLV surface. This is achieved using the following test criteria: $0 \leq |X_{Lqj}| \leq w/2$ and $-H \leq Y_{Lqj} \leq 0$.

Using computer coordinates $X_{eqj}$ and $Y_{Lqj}$, the computer o then computes the address values $A(x_{Lqj}, y_{Lqj})$ at each intersection point $Q_{Lj}$. In the ideal case where each pixel has a very high resolution, there generally will be a one-to-one correspondence between a particular coordinate pair and a particular pixel. In many applications, however, pixel resolution will be less then ideal and a number of clustered coordinates can be assigned to a particular pixel on the LCLV surface. Such relationships between coordinate pairs and pixels can be represented in a table which is stored in memory and readily accessible by the computer.

Finally, as indicated in step H, controller/driver 16 uses address values $A(x_{Lqj}, y_{Lqj})$ and intensity reduction data $m(P_j)$ to address and actively drive the particular pixels of the LCLV panel, thereby selectively reducing the intensity of incident light rays propagating along line $r_{Lj}$. As steps D through H are being performed, steps D' through H' are also performed for points $P_j$ in the imaged scene. In this way computed pixels through which light rays $r_{rj}$ intersect are electrically addressed and actively driven so as to reduce the intensity of light rays propagating towards the driver's right eye.

Referring to FIGS. 6 through 8B, the second illustrated embodiment of the electro-optical system of the present invention, will be described.

Figure 6:
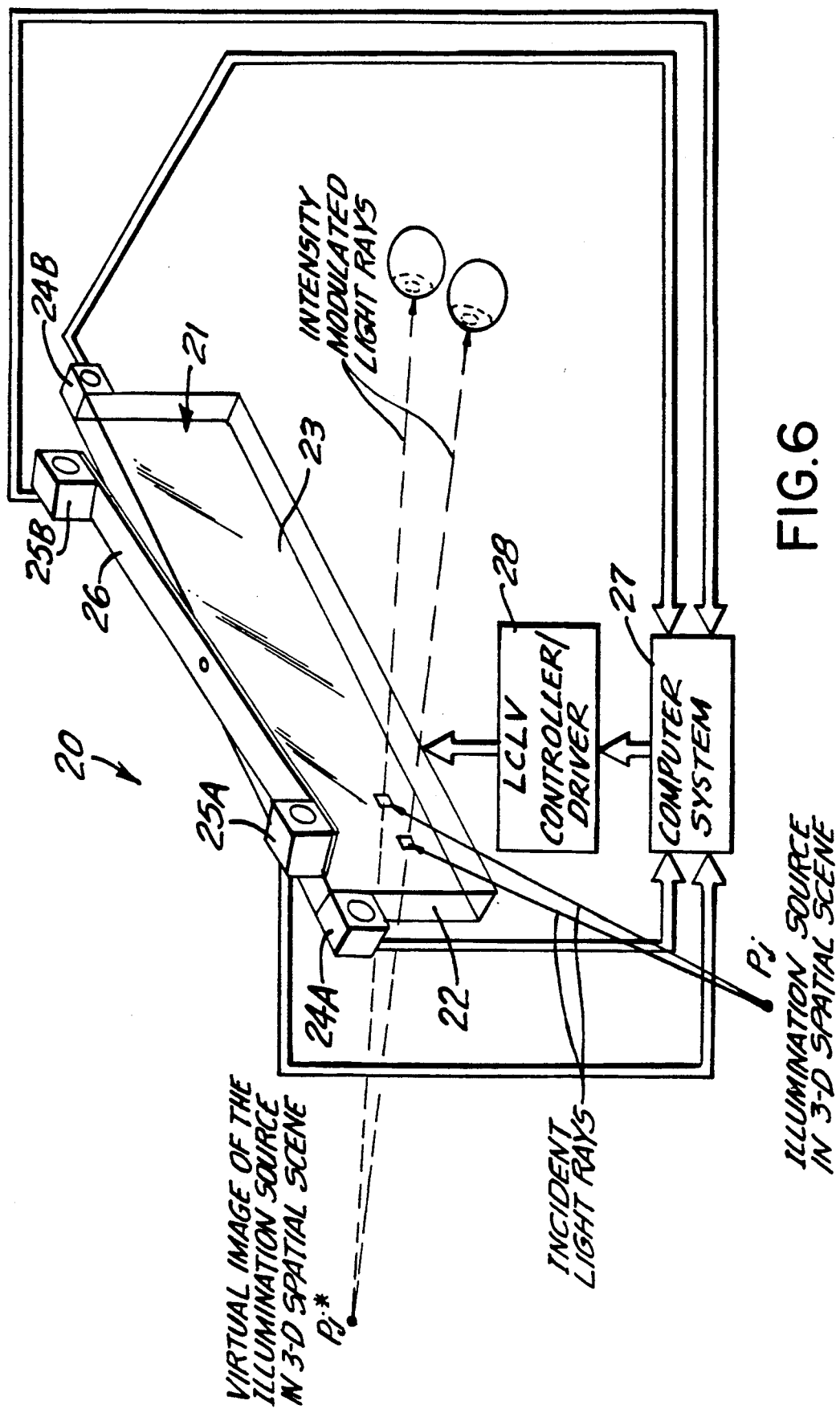
FIG. 6 is a schematic diagram illustrating the configuration of a second embodiment of the electro-optical system of the present invention, in which the light intensity reducing surface is a reflective-type liquid crystal light valve panel carrying a stereo scene camera subsystem for imaging spatial scenery within the field of view of an automobile driver, and a stereo pupil-tracking camera subsystem for measuring the position of the driver's pupils relative to the liquid crystal light valve panel.

As illustrated in FIG. 6, the electro-optical element of system 20 is in the form of an optically reflective LCLV panel 21. In this illustrated embodiment, reflective LCLV panel 21 is adapted for pivotal mounting inside an automobile at a position presently occupied by conventional rear-view mirrors above the dashboard. It may, however, be installed outside the automobile vehicle and function as a side view mirror. Preferably, the width of the reflective LCLV panel is about 30 centimeters, the height thereof about 10 millimeters and the pixel size about 2.5 centimeters, although these dimensions will understandably vary from embodiment to embodiment. In construction, LCLV panel 21 differs from LCLV panel 8 in that a light reflective coating 22 is applied on the rear of optically transparent surface 22 so that the LCLV panel will function like a mirror.

On opposite sides of the upper portion of LCLV panel 23, a pair of camera stations 24A and 24B similar to camera SO stations 13A and 13B in FIG. 2, are mounted to provide a stereo scene-imaging camera subsystem which images spatial scenery within the driver's field of view through the rear window of the automobile. In order to determine the position of the pupils of the driver's left and right eyes, a pair of infra-red camera substations 25A and 25B, similar to camera substations 9A and 9B in FIG. 2, are mounted along a rotatable platform 26 to form a pupil-tracking camera subsystem. To perform the data processing functions described in connection with the system of FIG. 2, electro-optical system 20 also includes a computer system 27 and an LCLV controller/driver 28 operably associated as shown in FIG. 6.

Figure 7:
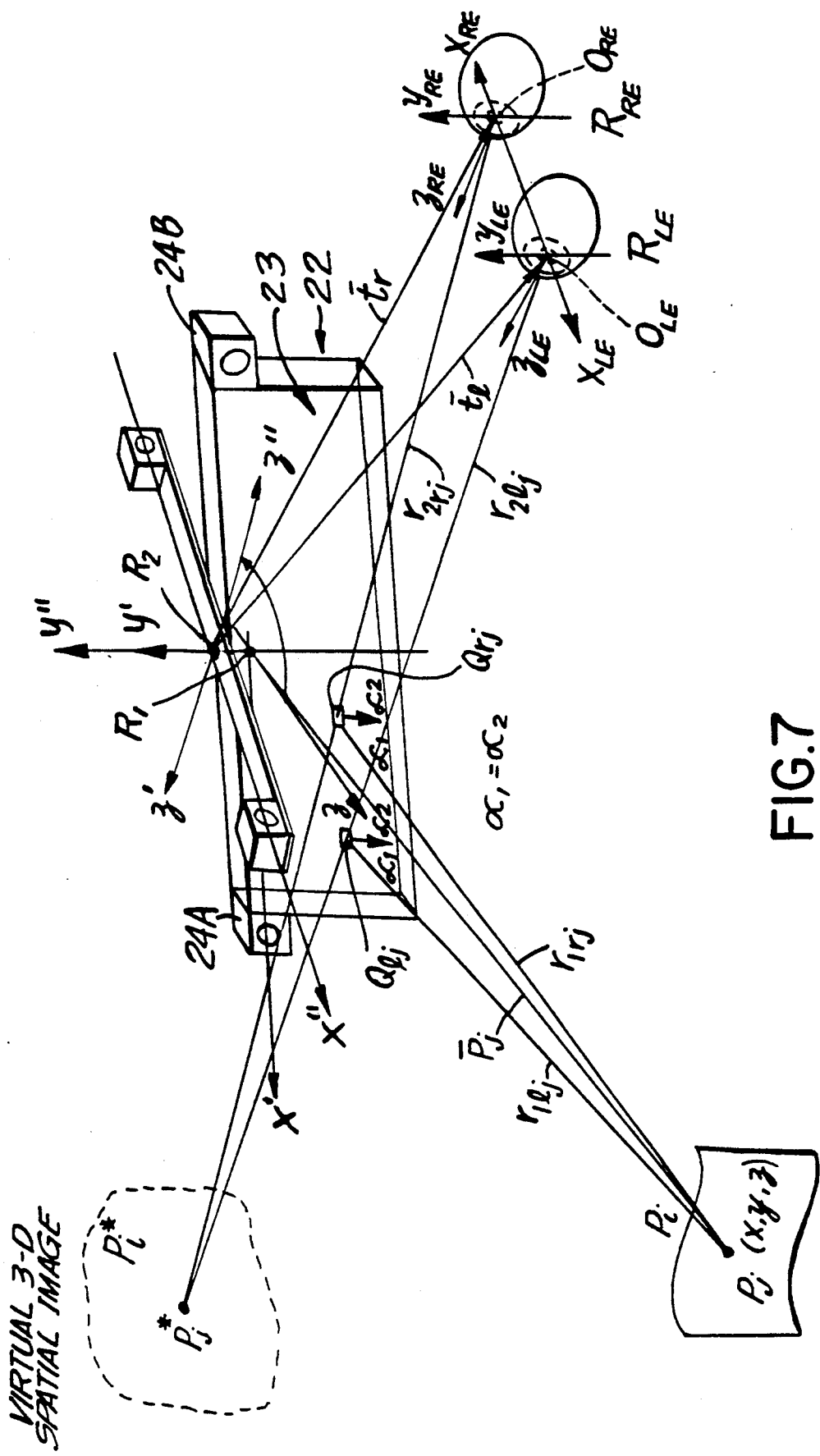
FIG. 7 is a schematic diagram illustrating the operation of the electro-optical system of FIG. 6, as light rays propagate from a point of illumination in the spatial scene, through the liquid crystal light valve and then intensity reduced prior to passing through the pupils of a driver's eyes.

In FIG. 7, a ray optics model is presented for electro-optical system of FIG. 6. As shown, coordinate system $R_1$, specified by x, y and z coordinate axes, is embedded within the reflective LCLV panel so that (i) the x-y plane of $R_1$ lies within the planar surface of the LCLV panel, (ii) the x axis is perpendicular to the optical axis of camera stations 24A and 24B, and (iii) the z axis is parallel with the optical axis of these camera stations. Coordinate system $R_2$, specified by x', y' and z' coordinate axes, is embedded within rotatable platform 26 so that (i) the x" axis is perpendicular to the optical axis of camera stations 25A and 25B, (ii) the y" axis is aligned with the y' axis of coordinate system $R_1$, and (iii) the center of origins of coordinate systems $R_1$ and $R_2$ spatially coincide. In order to measure the degree of rotation that coordinate system $R_1$ has undergone with respect to coordinate system $R_2$ at any particular positioning of the pupil-tracking camera subsystem, an optical encoder (not shown) is provided at the rotational axis between platform 26 and reflective LCLV panel 23. Data from the optical encoder regarding the relative rotation between coordinate systems $R_1$ and $R_2$ is provided to computer system 27 for processing in a manner to be described hereinafter.

Disposed at the center of the pupil of the driver's left eye is the origin of coordinate system $R_{LE}$ which is specified by axes $x_{Le}$, $y_{Le}$ and $z_{Le}$, with the $z_{Le}$ axis aligned with the optical axis of the driver's left eye. Disposed at the center of the pupil of the driver's right eye is the origin of coordinate system $R_{RE}$ which is specified by axes $x_{re}$, $y_{re}$ and $z_{re}$ with the $z_{re}$, axis aligned with the optical ID axis of the driver's right eye and the $x_{re}$ axis aligned with the x" axis of coordinate system $R_{Le}$. As shown, the position of origin $O_{Le}$ of coordinate system $R_{LE}$ is specified by position vector $t_L$ defined in coordinate system $R_c$. The origin $O_{Re}$ of coordinate system $R_{RE}$ is specified by position vector $t_r$ also defined in coordinate system $R_c$. Points $P_i$ in the spatial scene and virtual points $P_i^*$ behind the reflective LCLV panel are both specified by $x_i$, $y_i$, and $z_i$ coordinates in coordinate system $R_c$. Virtual points $P_i^*$ in the imaged scene having an intensity above a predetermined threshold are designated as Pixel and their position in coordinate system $R_c$ is specified by coordinates $x_j$, $y_j$, and $z_j$.

A light ray propagating from a point $P_j$ in the spatial scene and passing through the pixel surface of LCLV panel 23 to point $Q_{Lj}$ (enroute to the driver's left pupil) is specified by a 3-D line equation, $r_{1Lj}$. The path of the light ray reflecting off the reflective layer at point $Q_{Lj}$, towards the pupil of the driver's left eye, is specified by a 3-D line equation, $r_{2Lj}$. In accordance with the laws of physics, the angle of incident $\alpha_1$ of the incident light ray is equal to the angle of reflection $\alpha_2$ when measured from the normal vector $n_{Lj}$ at point $Q_{Lj}$. Similarly, a light ray propagating from point $P_j$ in the scene and passing through the pixel surface of LCLV panel to point $Q_{rj}$ (en route to the driver's right pupil) is specified by a 3-D line equation, $r_{rj}$. The path of the light ray reflecting off the reflective layer at point $Q_{rj}$, towards the pupil of the driver's right eye, is specified by a 3-D line equation, $r_{2rj}$. At point $Q_{rj}$, the angle of incidence $\alpha_1$ is equal angle of reflection oz when measured from the normal vector $n_{rj}$ at point $Q_{rj}$.

As the driver views a spatial scene of upcoming traffic through the automobile rear window (i.e., by perceiving light reflected off the reflective LCLV panel), a number of steps are repeatedly performed by the intelligent electro-optical system. In this way, while the driver operates the automobile, light reducing pixel locations are automatically determined, electrically addressed and actively driven on a real-time basis reducing glare associated with upcoming headlights.

Figure 8A:
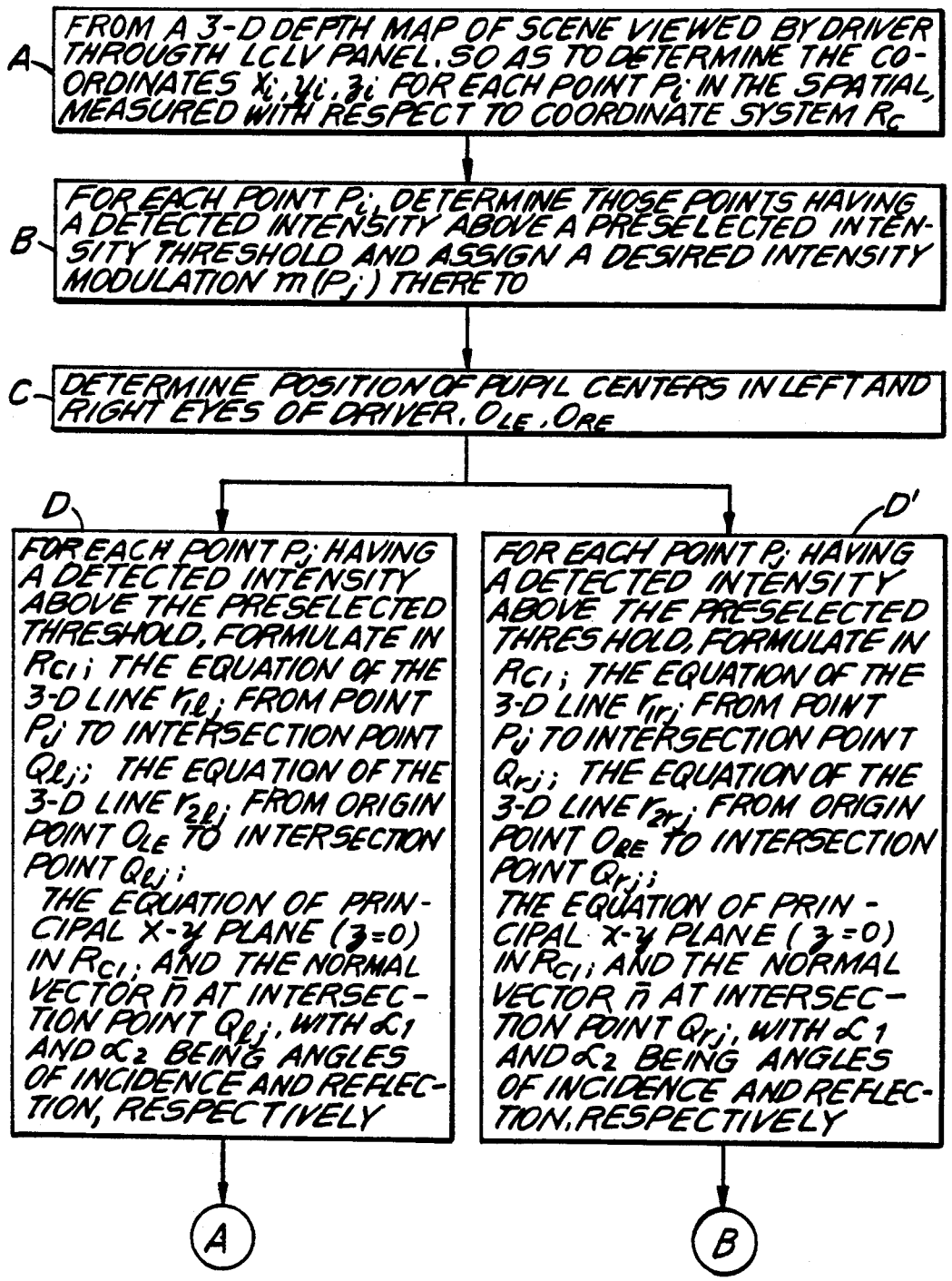
FIG. 8A and 8B is a flow chart showing the steps performed in determining the pixel locations of the liquid crystal light valve panel of the system of FIG. 6, and which are electrically addressed and controlled when reducing the intensity of light rays propagating from points of illumination in the spatial scene, toward the eyes of the driver.
Figure 8B:
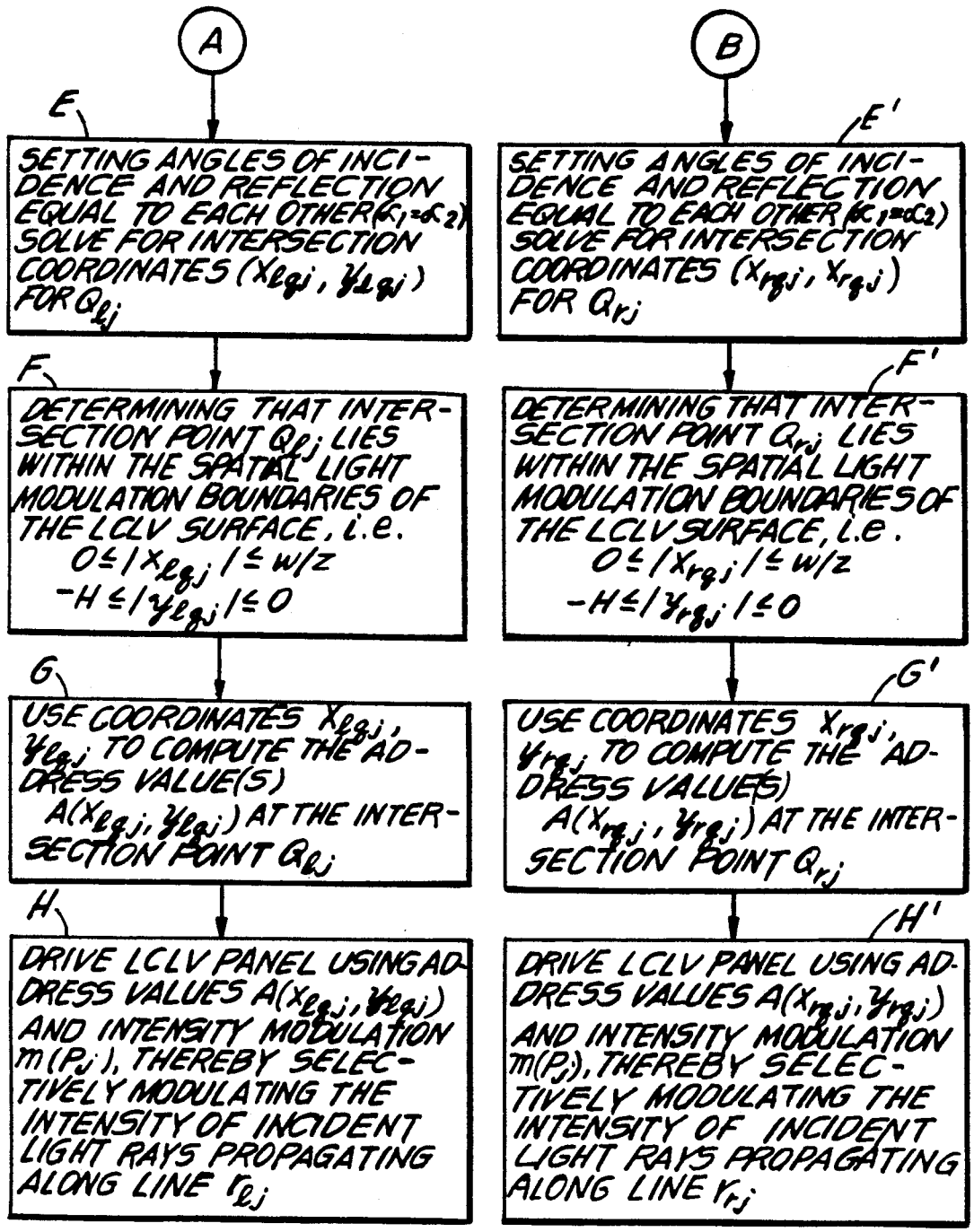

In FIGS. 8A and 8B, a generalized process is described for automatically reducing the intensity of light rays reflecting off the reflective layer of the LCLV panel, towards the driver's eyes. As indicated at blocks A, B and C, coordinate data regarding points $P_i$ in the scene is gathered, the data processed to detect high intensity points $P_j$ in the viewed scene, and the position of the driver's pupils are determined in a manner similarly described in connection with the system of FIG. 2. Then the sequence of steps D through H and D' through H' are performed in a parallel fashion in order to compute the x and y coordinates of the intersection points $Q_{Lj}$ and $Q_{rj}$, which coincide with each high intensity point $P_j$ in the viewed scene. Using this coordinate data, the corresponding pixels are electrically addressed and actively controlled to reduce the intensity of incident light rays, thereby eliminating glare.

Referring to FIGS. 9 through 11C, the third illustrated embodiment of the electro-optical system of the present invention will be described.

Figure 9:
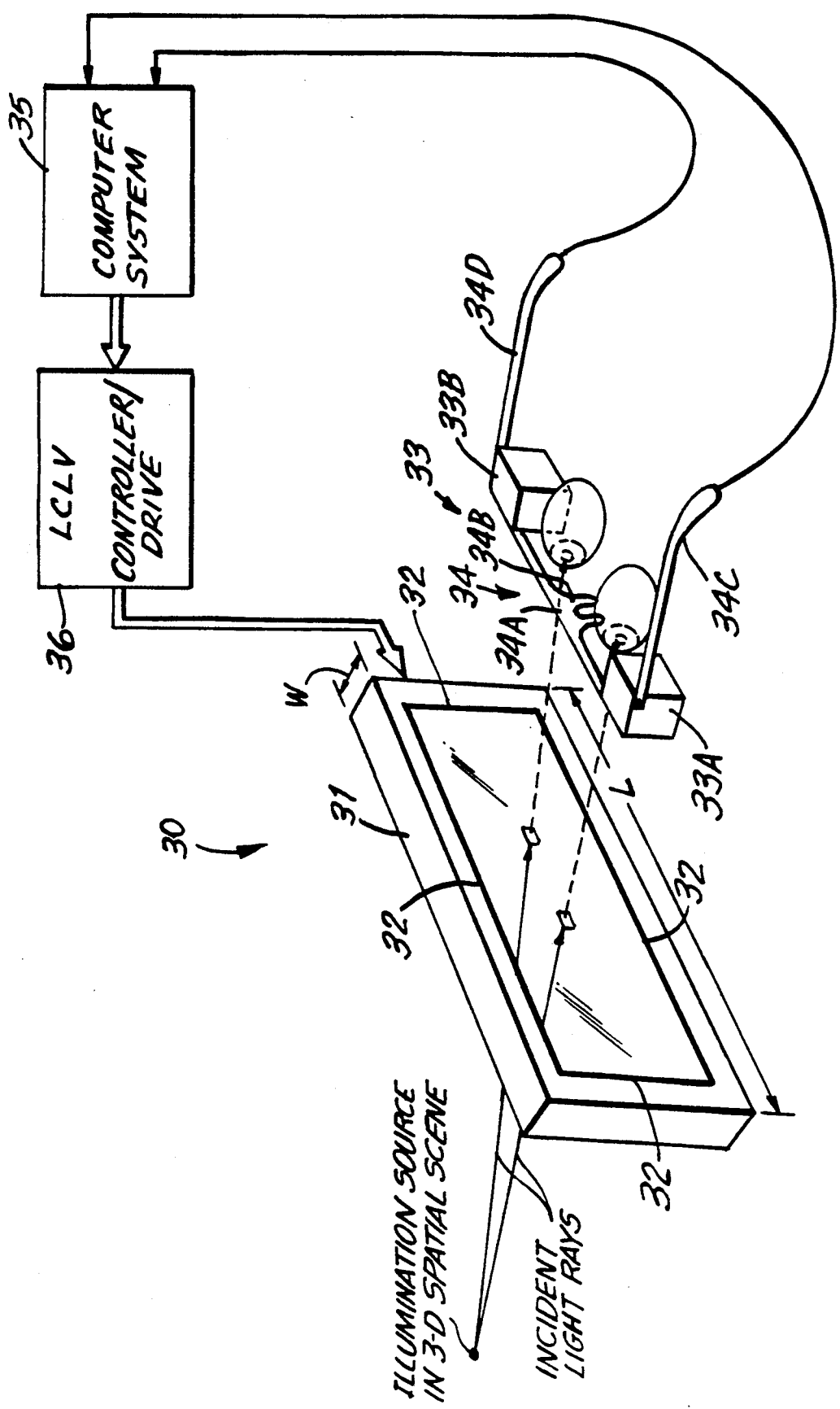
FIG. 9 is a schematic diagram illustrating the configuration of a third embodiment of the electro-optical system of the present invention, in which the light intensity reducing surface is an optically transparent liquid crystal light valve, and the driver carries a stereo scene imaging camera subsystem on his head for imaging for spatial scenery within the driver's field of view.

As illustrated in FIG. 9, the electro-optical element ID of system 30 is in the form of an optically transparent LCLV panel 31 adapted for pivotal mounting inside an automobile above the dashboard in a manner similar to a sunvisor. The LCLV panel has a width W, a length L and a rectangular border 32 surrounding the pixels of the panel. In night time glare reduction applications, pixel border 32 can be a luminous band realized by an optical fiber inlaid within a channel formed about the pixel perimeter. When light, from a source within the LCLV panel, is transmitted through the optical fiber, a rectangular band of low-level illumination is produced therefrom. In day time glare reduction applications, a black rectangular shaped pixel border, disposed against a reflective backing, can be provided for visually indicating the boundaries of the pixelled surface.

In order to acquire image(s) of oncoming traffic as seen by the driver along his or her field of view through the optically transparent LCLV panel, the driver wears a scene-imaging camera subsystem 33 embodied, for example, in a camera support frame 34 resembling the frame of a conventional pair of eyeglasses. As illustrated, the camera support frame has a bridge portion 34A with a nose bearing surface 34B and a pair of stems 34C and 34D which are adapted to encircle the driver's ears. In this embodiment, the scene-imaging camera subsystem comprises a pair of camera stations 33A and 33B disposed at opposite ends of the bridge portion. Acquired image data from the CCD image detection array in each camera station is transmitted through stems 34C and 34D to a computer 35 for processing in a manner described hereinabove. As will be described in greater detail hereinafter, the primary function of the computer system is to compute the addresses of pixels which are to be electrically addressed and actively driven so as to reduce the intensity of incident light rays from intense sources of illumination that have been detected in the acquired images of the scene being viewed by the automobile driver through the LCLV panel.

Figure 10:
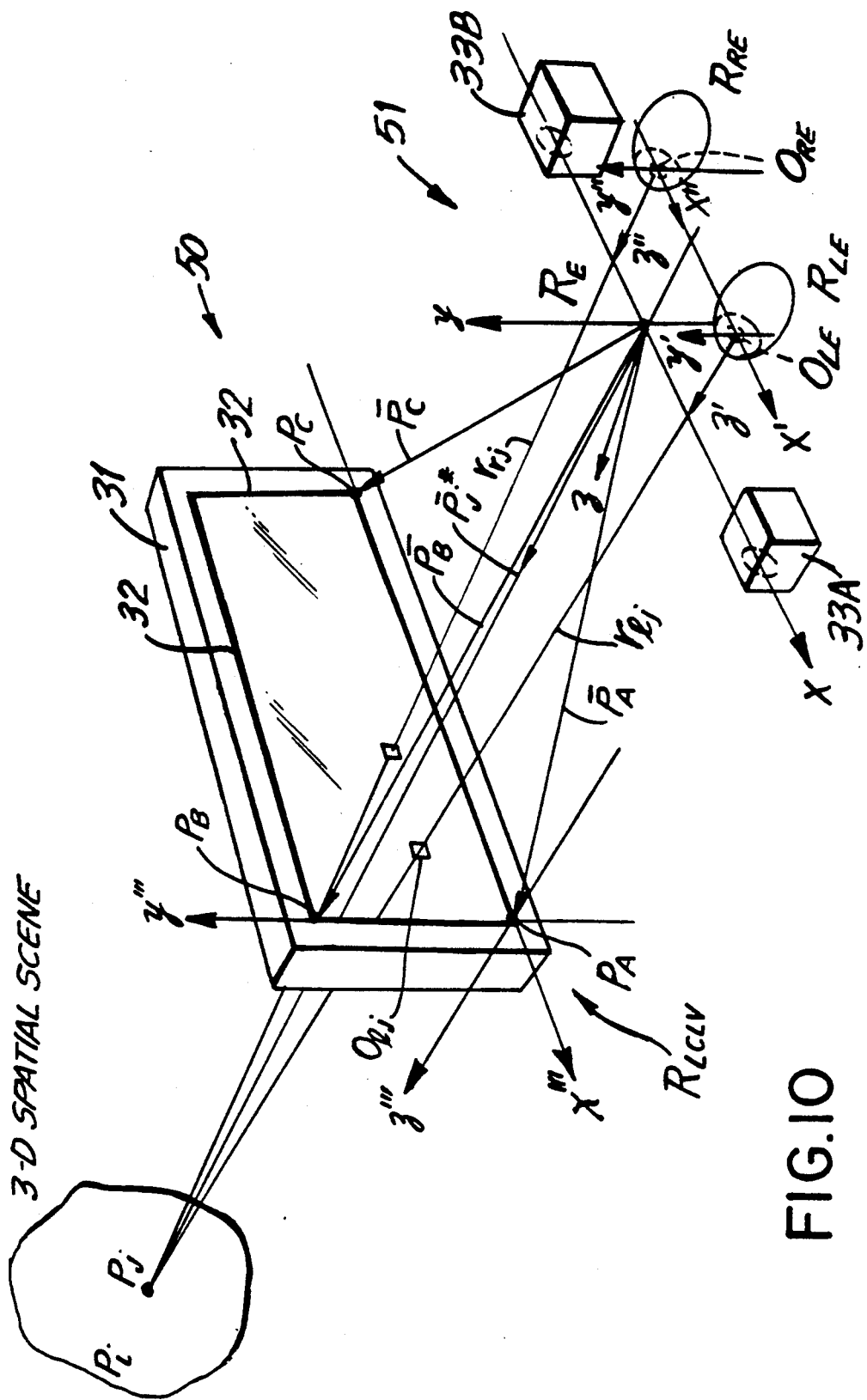
FIG. 10 is a schematic diagram illustrating the operation of the electro-optical system of FIG. 9 as light rays propagate from a point of illumination in the spatial scene through the liquid crystal light valve panel and then intensity reduced prior to passing through the pupils of a driver's eyes.

In FIG. 10 a ray optics model is presented for the electro-optical system of FIG. 9. As shown, coordinate system $R_c$ is embedded within the camera support frame so that (i) the x axis of is perpendicular to the optical axis of each camera station 33A and 33B, and (ii) the z axis is parallel with the optical axis of the camera stations. Disposed at the center of the pupil of the driver's left eye is the origin of coordinate system $R_{LE}$, which is specified by axes x', y' and z', with the z' axis aligned with the optical axis of the driver's left eye. Disposed at the center of the pupil of the driver's right eye is the origin of coordinate system $R_{RE}$ which is specified by axis x'', y'' and z'', with the z'' axis aligned with the optical axis of the drivers right eye, and the x'' axis aligned with the x' axis of coordinate system $R_{LE}$. The position of the origins of coordinate systems $R_{Le}$ and $R_{re}$, relative to coordinate system $R_c$, will vary slightly from one automobile driver to another, but can be simply determined and related by a homogenous transformation T. Determining transformation matrix T can be achieved by a calibration procedure, much like fitting a pair of eyeglasses to a person's head. The procedure involves (i) determining the coordinates of points $O_{ie}$ and $O_{re}$ (relative to coordinate system $R_c$) using stereo image acquisition and analysis described above, and (ii) using such coordinates to compute transformation matrices for these coordinate systems.

As illustrated in FIG. 1, coordinate system $R_{LCLV}$, specified by principal axes x''', y'' and z'' , is embedded within the LCLV panel so that the x-y plane of $R_{LCLV}$ lies within the pixel plane of the LCLV panel, and (ii) the center or origin of the coordinate system $R_{LCLV}$ coincides with the point at which the left vertical pixel border intersects with the lower horizontal pixel border. Points $P_i$ in the scene are specified by coordinates $x_i$, $y_i$, $z_i$ measured in coordinate system $R_c$, and points in the scene having an intensity above a predetermined threshold are designated as $P_j$. The position of points $P_j$ are specified by coordinates $x_j$, $y_j$, $z_j$ measured in coordinate system $R_c$.

As the automobile driver views oncoming traffic through the automobile front window, a number of steps are repeatedly performed by intelligent electro-optical system 50, permitting the driver to operate his vehicle while light reducing pixel locations are automatically determined and electrically addressed and actively driven on a real-time basis.

Figure 11A:
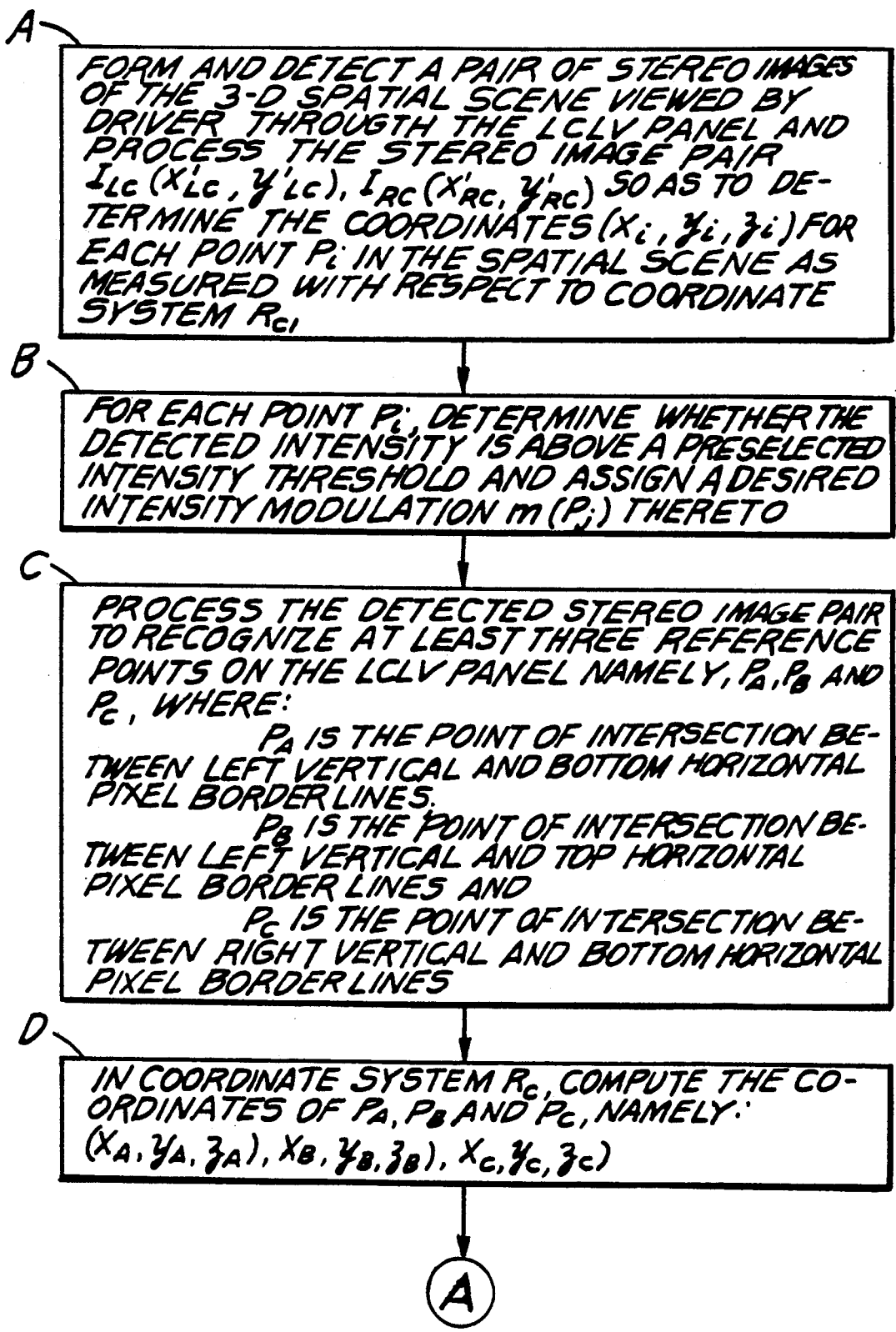
FIG. 11A, 11B and 11C is a flow chart showing the steps performed in determining the pixel locations of the liquid crystal light valve panel of the system of FIG. 9, which are electrically addressed and actively controlled in order to reduce the intensity of light rays propagating from points of illumination in the spatial scene, towards the eyes of the driver.
Figure 11B:
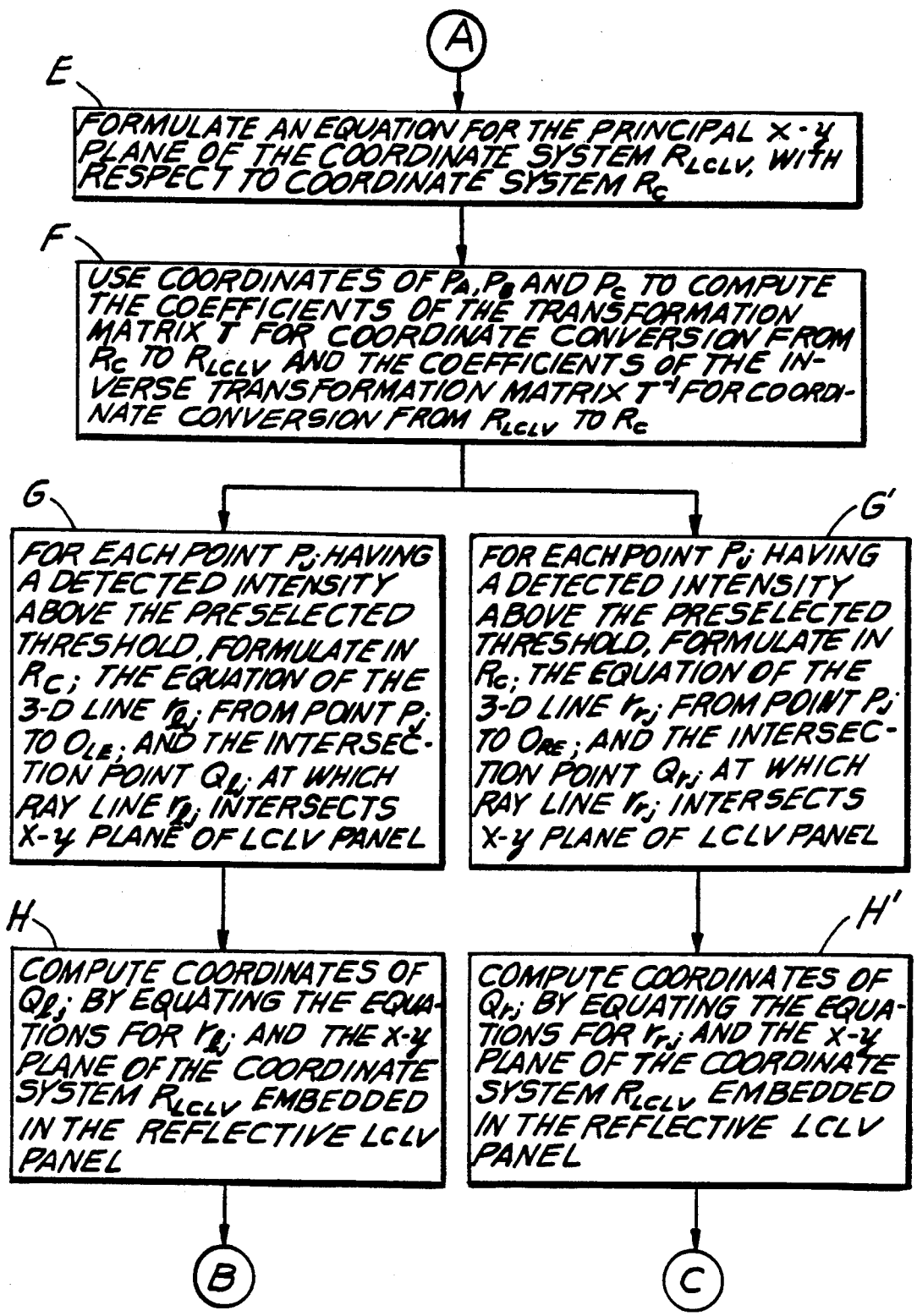
Figure 11C:
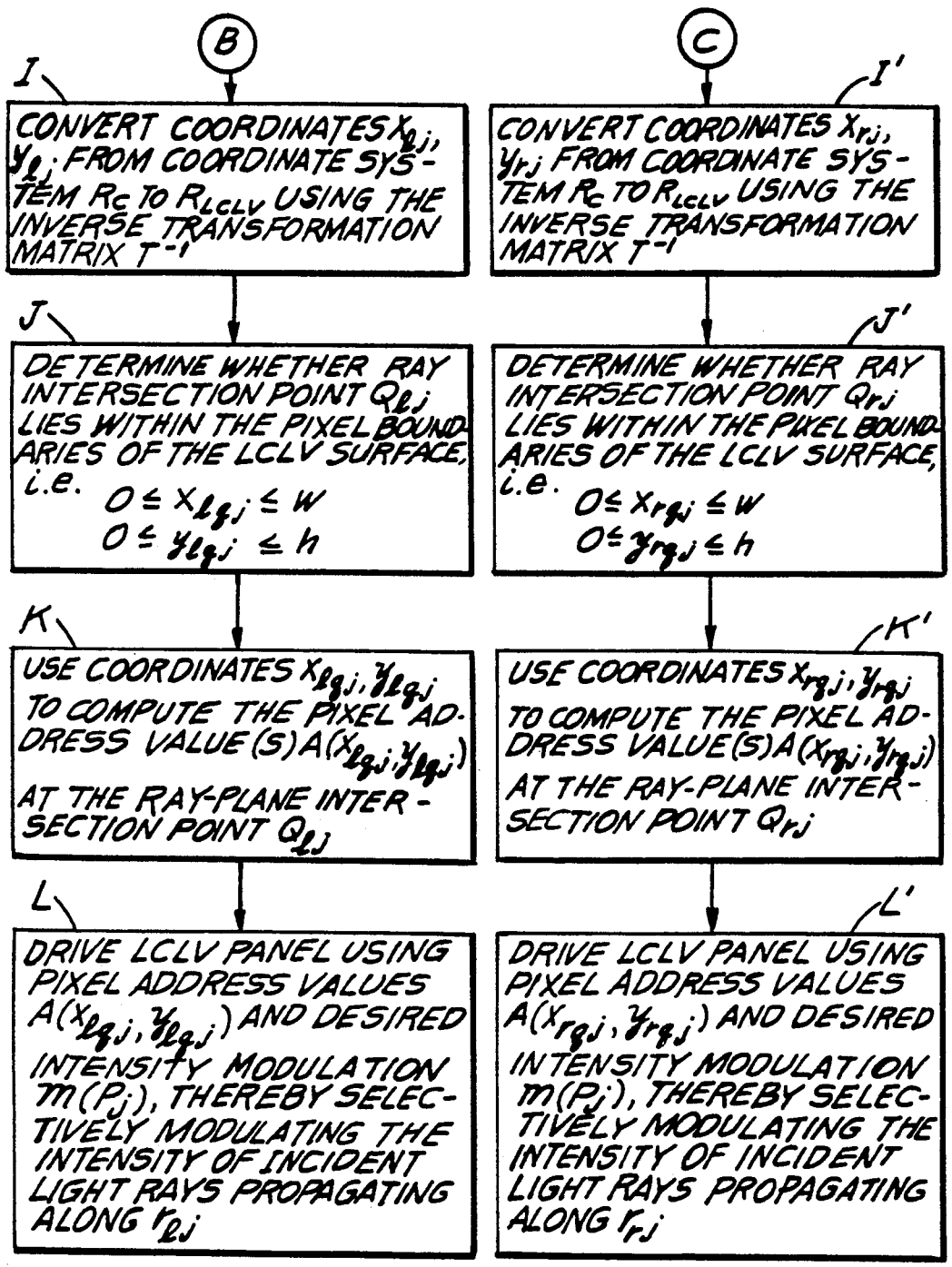

In FIGS. 11A through 11C, a generalized process is described for automatically reducing the intensity of light rays which propagate through the optically transparent surface of the LCLV panel, towards the driver's eyes. As indicated at block A of FIG. 11A, the camera system acquires and buffers a pair of stereo images of the spatial scene viewed by the automobile driver through the LCLV panel. The acquired stereo image pair is then processed to determine the coordinates ($x_i$, $y_i$, $z_i$) for each point $P_i$ represented in the image(s) of the spatial scene. As indicated at block B, the computer determines for each point $P_i$ whether the detected light intensity is above a preselected intensity threshold, and if so assigns to each such point $P_j$ a desired intensity reduction m($P_j$).

As indicated as Block C, the computer then processes once again the acquired stereo image pair in order to recognize at least three selected points on the LCLV panel, namely $P_A$, $P_B$ and $P_C$ which lie on luminous pixel border 32. As illustrated in FIG. 10, $P_A$ is selected as the point of intersection between left vertical and bottom horizontal pixel border lines; $P_B$ is selected as the point of intersection between left vertical and top horizontal pixel border lines; and $P_C$ is selected as the point of intersection between right vertical and bottom horizontal pixel border lines. As indicated at B block D, the computer uses these recognized points in the acquired stereo image pair to compute the coordinates of recognized points $P_A$, $P_B$ and $P_C$, specifically: ($x_A$, $y_A$, $z_A$), ($x_b$, $y_B$, $z_B$) and $x_C$, $y_C$, $z_C$). Thereafter, as indicated in Block E, the computer formulates the equation for the principal x-y plane of coordinate system $R_{LCLV}$, with respect to coordinate system $R_C$. Then using the coordinates of the recognized points $P_A$, $P_B$ and $P_C$, the computer computes the coefficients of the transformation matrix T for coordinate conversion from $R_C$ to $R_{LCLV}$, and also the coefficients of the inverse transformation matrix $T^{-1}$ for coordinate conversion from $R_{LCLV}$ to $R_C$.

At this stage of the process, the system performs in parallel the steps indicated at Block G through L for left eye ray optics, and Blocks G' through L' for right eye ray optics. Specifically, at Block G the computer formulates (in coordinate system $R_c$) for each point $P_j$, the equation of the 3-D lines $r_{Lj}$ from point $P_j$ to origin point $O_{Le}$, and the intersection point $Q_{Lj}$ at which lines $r_{Lj}$ intersects the plane or surface of the LCLV panel. At Block H, the computer computes the coordinates ($x_{Lj}$, $y_{Lj}$) of intersection point $Q_{Lj}$ by equating the equations for $r_{Lj}$ and the x-y plane of coordinate system $R_{LCLV}$. At Block I, the computer converts coordinates $x_{Lj}$, $y_{Lj}$ from coordinate system $R_c$ to $R_{LCLV}$ using the inverse transformation matrix T-1. At Block J, the computer determines whether or not the coordinates of intersection point $Q_{Lj}$ lie within the pixel boundaries of the LCLV panel, i.e., whether or not $0 \leq X_{Lqj} \leq W/2$ and $0 \leq Y_{Lqj} \leq h$ for all values of j in the acquired stereo image pair. Then, as indicated at Block K, the computer uses coordinates $x_{Lqj}$, $y_{Lqj}$ to compute address value(s) A($x_{Lqj}$, $y_{Lqj}$) at each ray-plane intersection point $Q_{Lj}$. Then to complete the process, the controller/driver addresses the pixels with pixel address value(s) A($x_{Lqj}$, $y_{Lqj}$) and drives each addressed pixel with its desired intensity reduction m($P_j$), thereby selectively reducing the intensity of incident light rays propagating along path $r_{Lj}$. When the steps indicated at Blocks G' through L' are carried out, intensity reduction of light rays propagating along path $r_{rj}$ is achieved.

Referring to FIGS. 12 through 14C, the fourth illustrated embodiment of the electro-optical system of the present invention, will be described.

Figure 12:
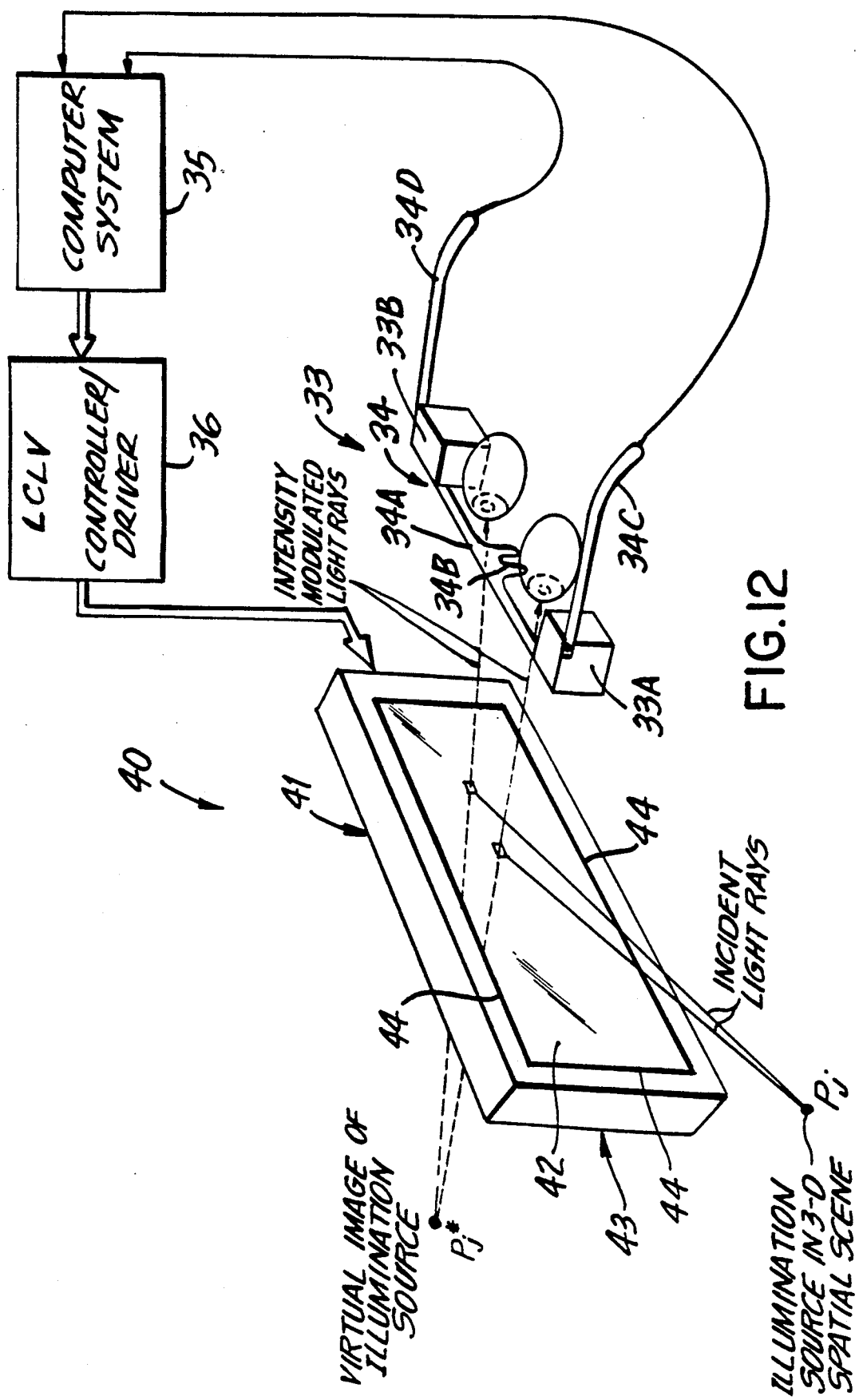
FIG. 12 is a schematic diagram illustrating the configuration of a fourth embodiment of the electro-optical of the present invention, in which the light intensity reducing surface is a reflective-type liquid crystal light valve panel, and the driver carries a stereo scene imaging camera subsystem on his head for imaging spatial scenery within the driver's field of view.

As illustrated in FIG. 12, the electro-optical element of system 40 is in the form of an optically reflective LCLV panel. This LCLV panel can be adapted for pivotal mounting, for example, inside an automobile at a position presently occupied by the rear-view mirror above the dashboard, or alternatively, outside the automobile as a side view mirror. The construction of reflective LCLV panel 41 is similar to the panel described in the second illustrative embodiment. In addition to an optically transparent LCLV surface 42 and reflective surface 43, reflective LCLV panel 41 has a rectangular shaped luminous border 44, as described in connection with the second illustrative embodiment above. All other components of the electro-optical system are similar to that depicted in connection with the third illustrative embodiment of the present invention.

Figure 13:
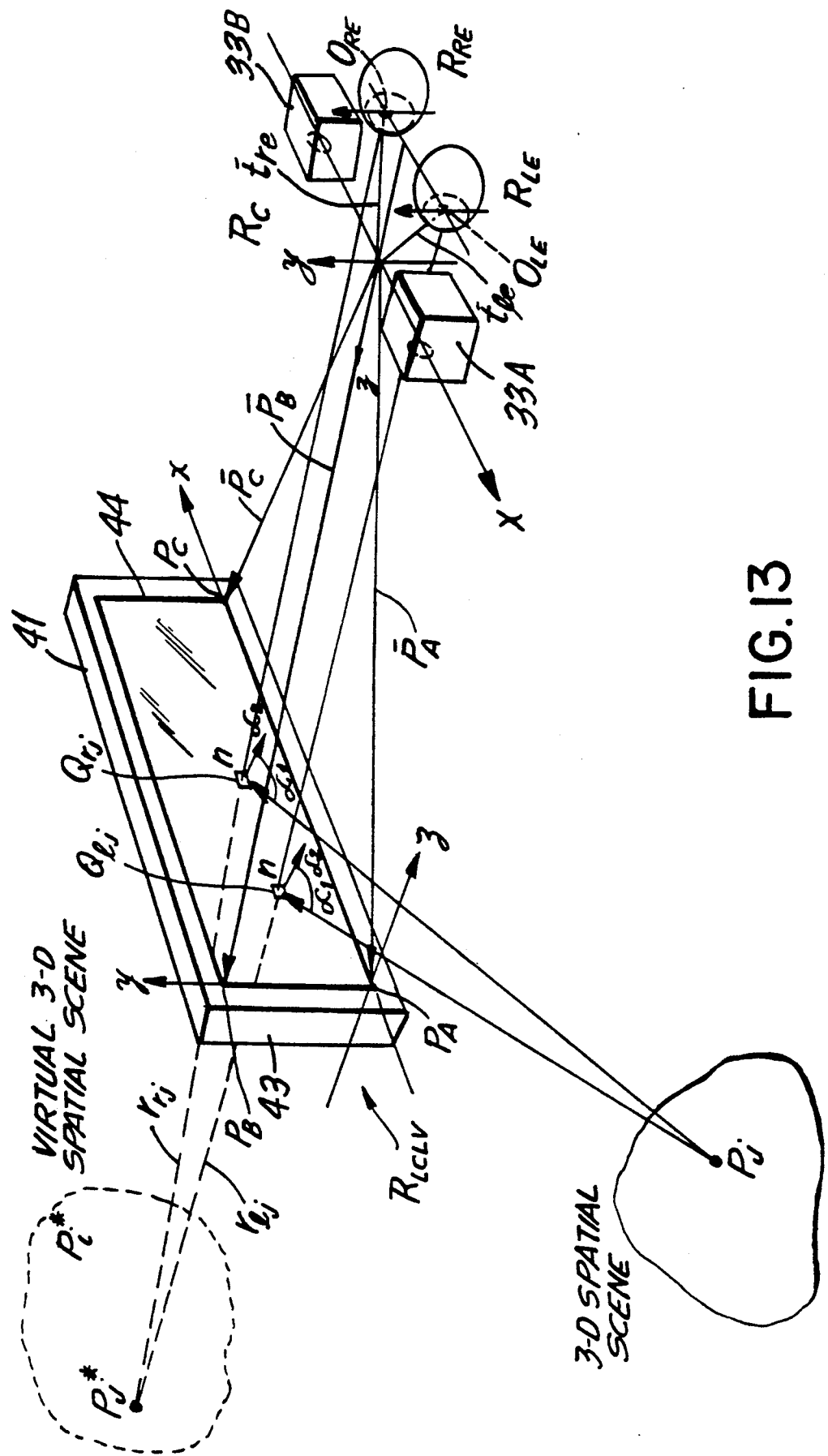
FIG. 13 is a schematic diagram illustrating the operation of the electro-optical system of FIG. 12, as light rays propagating from a point of illumination in the spatial scene reflects off the liquid crystal light valve panel and then intensity reduced prior to passing through the pupils of the driver's eyes.
Figure 14A:
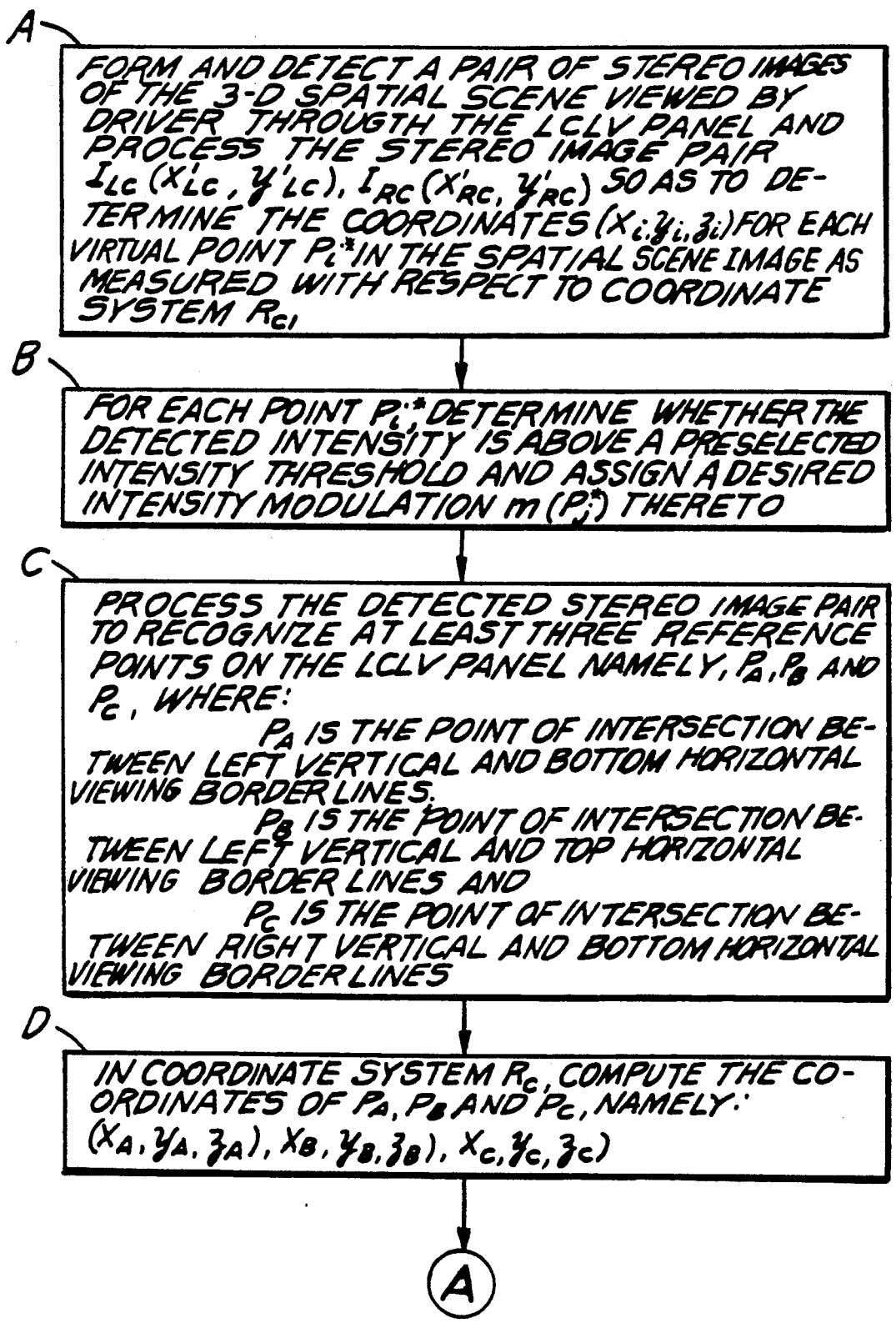
FIG. 14A, 14B and 14C is a flow chart showing the steps performed in determining in the pixel locations of the liquid crystal light valve panel of the system of FIG. 12, which are electrically addressed and actively controlled pixels in order to reduced the intensity of light rays propagating from points of illumination in the spatial scene, towards the eyes of the driver.
Figure 14B:
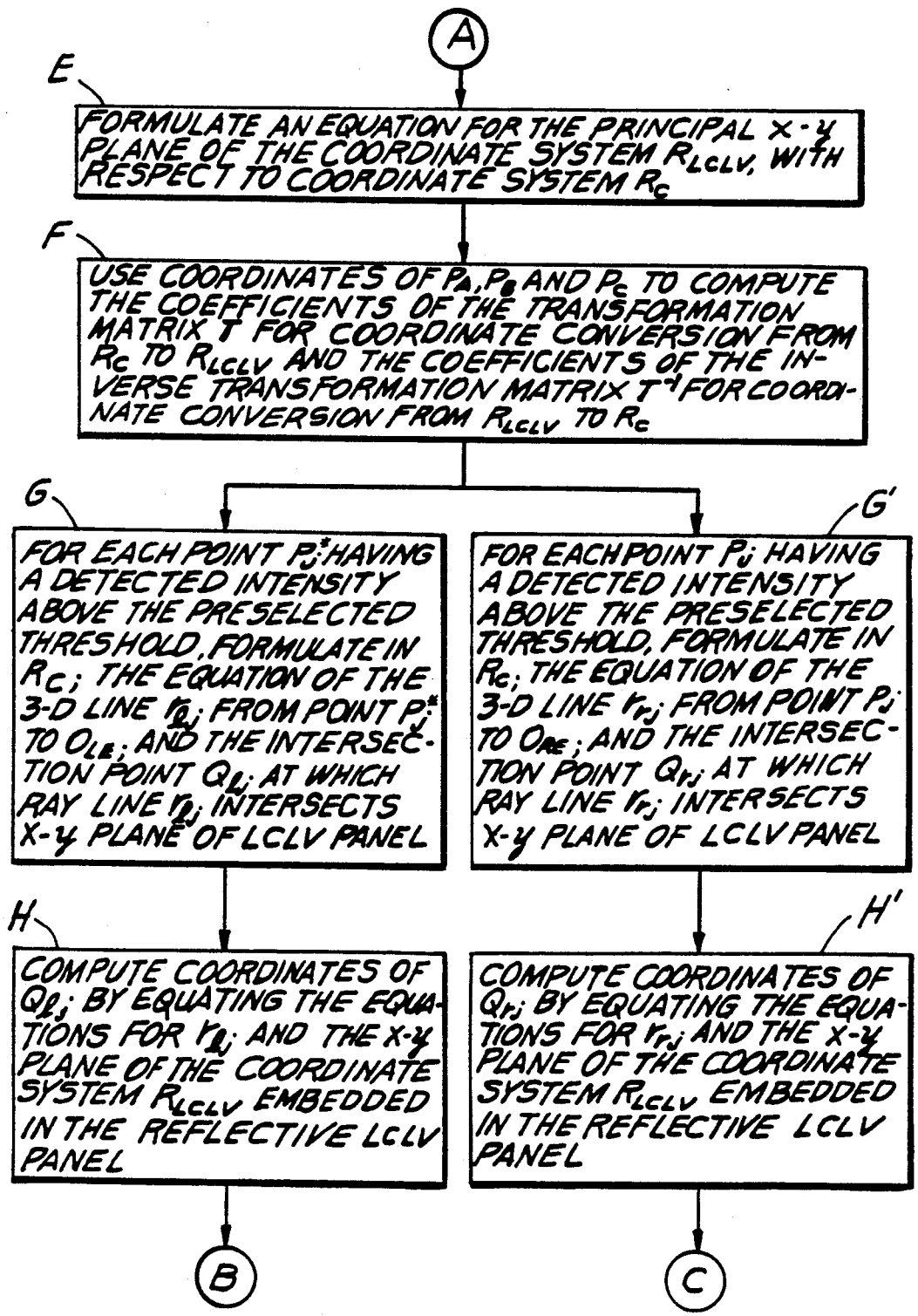
Figure 14C:
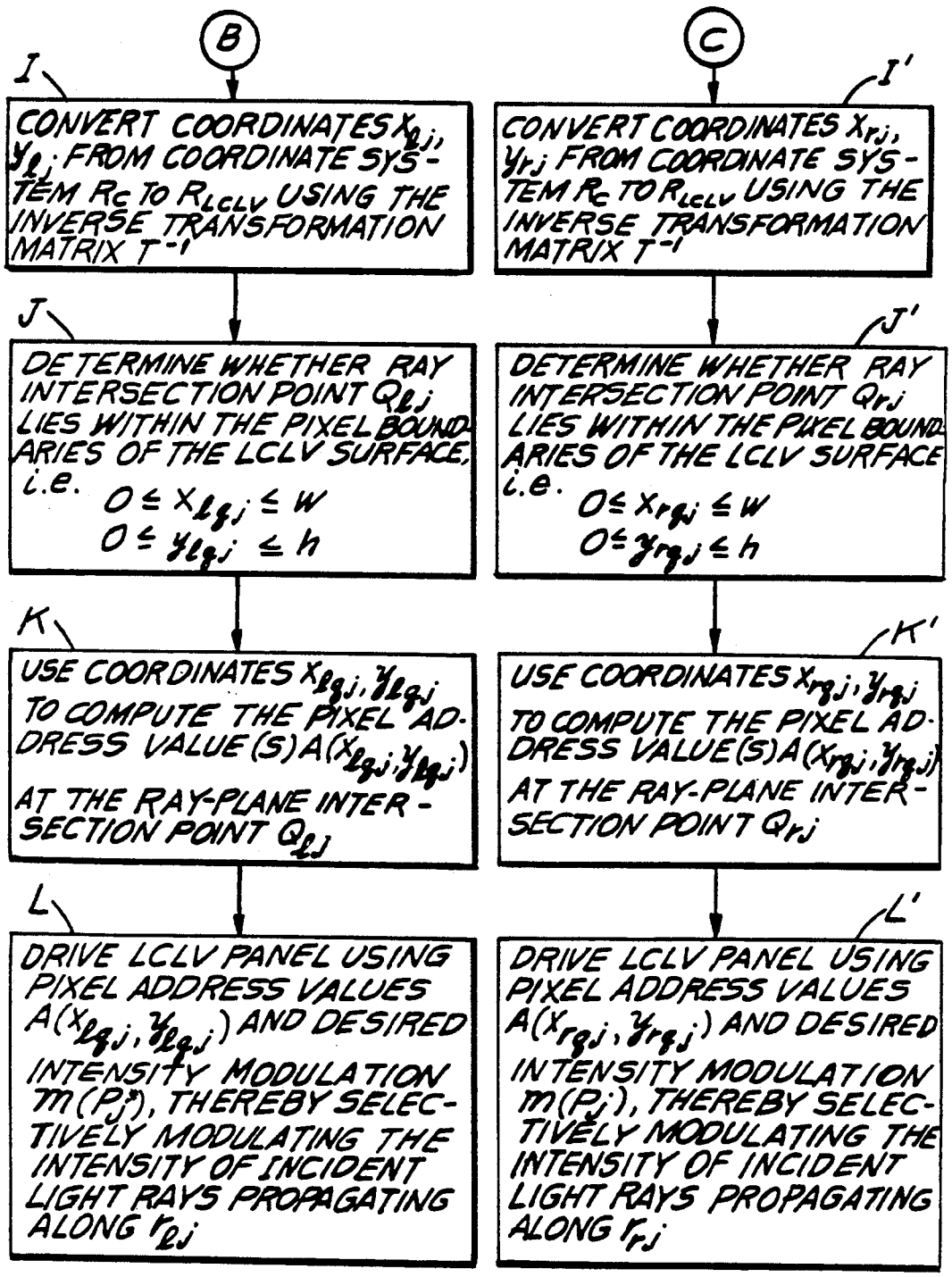

In FIG. 13, a ray optics model is presented for the electro-optical system of FIG. 12. In nearly all respects, this embodiment of the electro-optical system is modelled identical to the electro-optical system of the third embodiment of the present invention. The only difference is that the image of points $P_i$ and $P_j$ (designated as $P_i^*$ and $P_j^*$ respectively) are used to formulate the path that light rays transverse from their respect position in the spatial scene, towards the pupils of the left and right eyes of the automobile driver. Notably, this ray optics approach takes advantage of a particular relationship which holds true for a planar reflective surface, namely: that the distance from intersection point $Q_{Lj}$ to point $P_j^*$ equals the distance from point $Q_{Lj}$ to point $P_j$, and likewise the distance from point $P_i$ to point $Q_{rj}$ equals the distance from point $P_i^*$ to point $Q_{rj}$. Consequently, virtual points $P_i^*$ in acquired images of a spatial scene can be used in the process illustrated in FIGS. 11A through 11C. This process is depicted in FIGS. 14A through 14C, and is identical to the process of FIGS. 11A through 11C in all other respects.

In each of the four illustrative embodiments of the present invention described above, a general approach has been provided to the problem of modulating the amplitude of incident light rays using electrically addressable pixelled surface having controllable light transmittance. While these approaches provide a general solution to the problem over any range of system operations or configurations, there will be applications in which system constraints permit the use of computing techniques less complex in the computational sense.

Figure 15:
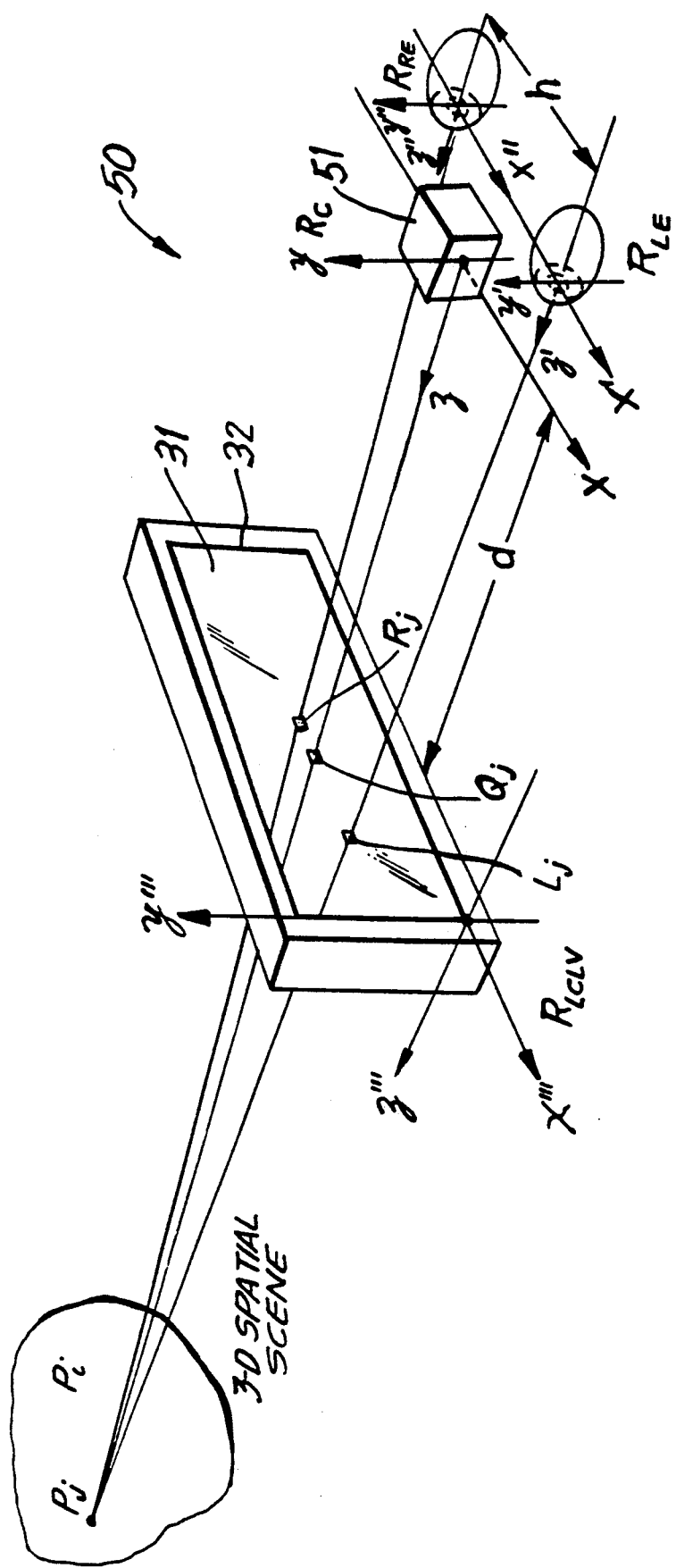
FIG. 15 is a schematic diagram of a fifth embodiment of the electro-optical system of the present invention, in which the light intensity reducing surface is a optically o transparent liquid crystal light valve panel carrying a monocular scene-imaging camera for imaging spatial scenery within the field of view of an automobile driver, and an eye and head tracking subsystem for measuring the position and orientation of the driver's eyes relative to the liquid crystal light valve panel.
Figure 15A:
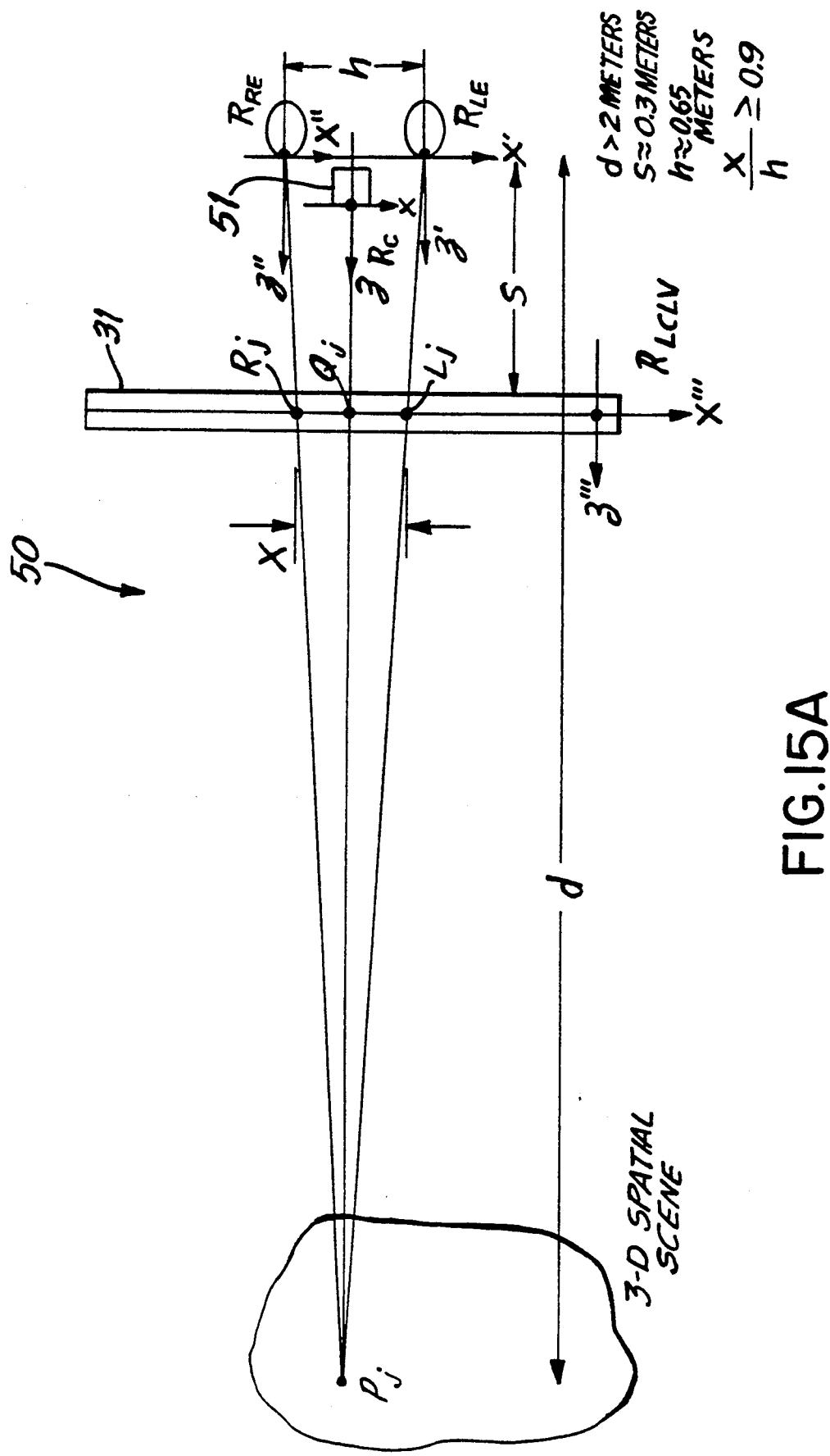
FIG. 15A is a plan view of the electro-optical system illustrated in FIG. 15.

FIG. 15, a ray optics model is presented for a fifth embodiment of the electro-optical system of the invention. As illustrated, the system is generally indicated by reference numeral 50. In this embodiment of the present invention, the automobile driver wears a single camera station 51 supported by a support frame similar to the one illustrated in FIG. 10. The camera station is operably connected to a computer which is interfaced with a controller/driver similar to that shown in FIG. 10. A coordinate system $R_c$, specified by principal axes x, y and z, is embedded in the camera station so that (i) the z axis is aligned with the optical axis of the camera station, and (ii) the origin of coordinate $R_c$ system is positioned at the principal plane of the image forming optics of the camera station.

Disposed at the center of the pupil of the driver's left eye is the origin of coordinate system $R_{LE}$ which is specified by axes x', y' and z' with the z' axis aligned with the optical axis of the driver's left eye. Disposed at the center of the pupil of the driver's right eye is the origin of coordinate system $R_{RE}$ which is specified by axis x'', y'', and z'', with the z', axis aligned with the optical axis of the driver's right eye, and the x'' axis aligned with the x' axis of coordinate system $R_{LE}$.

The position and orientation of the origins of coordinate systems $R_c$ and $R_{LCLV}$ are determined using a position and orientation tracking system well known in the art. Using such position and orientation data, a homogeneous transformation between coordinate systems $R_c$ and $R_{LCLV}$ can be computed and used to convert the coordinates specified in coordinate system $R_c$ to coordinates specified in coordinate system $R_{LCLV}$.

When using the electro-optical system of FIG. 15 in automotive applications, the distance S measured between the LCLV panel and the driver's pupils will be about 0.3 meters, and points of intense illumination $P_j$ will typically reside at a distances of 2 or more meters from the driver's pupils. In such cases, the ratio of x/h will be 0.9 or greater, indicating that incident light rays propagating through the LCLV panel to the driver's pupils will be approximately parallel. As will be described below, this condition permits simplification of the computing approach used in determining the ray-panel intersection coordinates, $L_j$ and $R_j$.

The simplified process involves first acquiring an image of the spatial scene within the driver's field of view using the camera system. The pixels of the acquired image are processed to detect intensity levels above a preselected threshold. Then, the x, y coordinates of each image pixel corresponding with point $P_j$ (having an intensity above the threshold) are converted from coordinate system $R_c$ to the coordinate system $R_{LCLV}$, embedded in the LCLV panel. This coordinate conversion step is achieved using the homogeneous transformation matrix computed above. The condition $x/h \geq 0.9$ justifies this step since the x, y coordinates of each intersection point $Q_j$ can be equated with the pixel coordinates on the camera's image detection plane, while introducing only a minor degree of error. From the coordinates of point $Q_j$, the coordinates of intersection points $L_j$ and $R_j$ can be computed using coordinate geometry and the average measure of interpupil distance, $h \approx 0.065$ meters. Having computed the coordinates of $L_j$ and $R_j$, the computer then computes the addresses $A(L_j)$ and $A(R_i)$ of corresponding pixels allowing for a sufficiently low pixel resolution in order to compensate for errors in $L_j$ and $R_j$. Using computed addresses $A(L_j)$ and $A(R_j)$ and intensity reduction data $m(P_j)$, the controller/driver addresses particular pixels and actively drives them to change their light transmittance to the desired value.

The above-described approximation technique for computing ray-plane intersection points $L_j$ and $R_j$ can be applied to reflection-type electro-optical systems as well.

Having described the illustrative embodiments of the present invention, several modifications are contemplated.

For example, the LCLV surface of the system hereof can be fashioned to the geometry of a windshield and-/or rear window of an automobile, while achieving the objects of the present invention.

A portable electro-optical system is envisioned, in which a monocular or stereo camera subsystem is embodied within a head supported frame having a pair of LCLV lenses, each disposed in front of one of the wearer's eyes. The resulting device can be worn as a pair of eyeglasses to block out solar glare during the day, and headlight glare at night.

The electro-optical system of the present invention may be installed within unmanned vehicles so as to protect image detecting components used in navigational systems. The electro-optical system of the present invention may operate at wavelengths within or outside the optical spectrum.

The present invention has been illustrated in applications in which glare produced by man-made illumination sources has been eliminated. However, glare and noise produced by solar sources can also be effectively reduced using the principles of the present invention.

While the particular embodiments shown and described above will be useful in many applications in the glare reduction art, further modifications of the present invention herein disclosed will occur to persons skilled in the art to which the present invention pertains. All such modifications are deemed to be within the scope and spirit of the present invention defined by the appended claims.

What is claimed is:

1. Apparatus for automatically reducing glare produced from a three-dimensional spatial scene by reducing the intensity of light rays propagating from points in the three-dimensional spatial scene towards an optical element having a field of view, said apparatus comprising:
    an electro-optical element having an optically transparent surface including a plurality of pixels through which the field of view of said optical element passes, each said pixel having a controllable light transmittance for selectively reducing the intensity of incident light rays propagating from one or more points in the three-dimensional spatial scene, through said pixel, then towards said optical element;
    image acquisition means for acquiring one or more images of said three-dimensional spatial scene within the field of view of said optical element;
    image processing means for processing said one or more acquired images and determining at which pixels the light transmittance is to be actively controlled in order to reduce the intensity of incident light rays by a selected amount before reaching said optical element; and
    control means for actively controlling the light transmittance of the determined pixels so that after incident light rays propagate through said determined pixels, said incident light rays propagate towards said optical element with an intensity reduced by said selected amount, so that glare produced from the three-dimensional spatial scene is automatically reduced.

2. The apparatus of claim 1, wherein said control means comprises means for electrically addressing and driving said determined pixels, and wherein the light transmittance of each said pixel is independently controllable.

3. The apparatus of claim 2, which further comprises an optical element tracking means for determining the position of said optical element with respect to said electro-optical element, and wherein said image acquisition means is stationarily positioned with respect to said electro-optical element.

4. The apparatus of claim 1, wherein said electro-optical element comprises an electrically addressable liquid crystal light valve, and wherein the light transmittance of each said pixel is independently controllable.

5. The apparatus of claim 4, wherein said optical element is the pupil of an eye which is free to move relative to said electro-optical element.

6. The apparatus of claim 5, which further comprises means for installing said electro-optical element above the dashboard of an automotive vehicle.

7. The apparatus of claim 2, which further comprises an optical element tracking means for determining the position of said optical element with respect to said electro-optical element, and wherein said image acquisition means is stationarily positionable with respect to said electro-optical element.

8. The apparatus of claim 7, wherein said electro-optical element comprises an electrically addressable liquid crystal light valve.

9. The apparatus of claim 8, wherein said optical element is the pupil of an eye which is free to move relative to said optical element.

10. The apparatus of claim 9, which further comprises means for installing said electro-optical element above the dashboard of an automotive vehicle.

11. The apparatus of claim 2, wherein said electro-optical element and said image acquisition means are stationarily positioned with respect to said optical element.

12. The apparatus of claim 11, wherein said optical element is the left and right eyes of a person, and wherein said electro-optical element comprises first and second electrically addressable liquid crystal light valve panels stationarily positionable with respect to said left and right eyes.

13. The apparatus of claim 1, wherein said electro-optical element further comprises a reflective layer adjacent said optically transparent surface so as to reflect incident light rays from behind said optically transparent surface.

14. The apparatus of claim 13, which further comprises an optical element tracking means for determining the position of said optical element with respect to said electro-optical element, and wherein said image acquisition means is stationarily positioned with respect to said electro-optical element.

15. The apparatus of claim 14, wherein said electro-optical element comprises an electrically addressable liquid crystal light valve surface.

16. The apparatus of claim 15, wherein said optical element is the pupil of an eye which is free to move relative to said electro-optical element.

17. The apparatus of claim 16, which further comprises means for installing said electro-optical element above the dashboard of an automotive vehicle.

18. The apparatus of claim 13, which further comprises an optical element tracking means for determining the position of said optical element with respect to said electro-optical element, and wherein said image acquisition means is stationarily positionable with respect to said electro-optical element.

19. The apparatus of claim 18, wherein said electro-optical element comprises an electrically addressable liquid crystal light valve surface.

20. The apparatus of claim 19, wherein said optical element is the pupil of an eye which is free to move relative to said optical element.

21. The apparatus of claim 20, which further comprises means for installing said electro-optical element above the dashboard of an automotive vehicle.

22. The apparatus of claim 13, wherein said electro-optical element and said image acquisition means are stationarily positioned with respect to said optical element.

23. A method for automatically reducing glare produced from a three-dimensional spatial scene by reducing the intensity of light rays propagating from points in the three-dimensional spatial scene towards an optical element having a field of view, said method comprising the steps:
  a) providing an elector-optical element at a desired distance from said optical element so that the field of view of said optical element passes through said electro-optical element and in the direction of the three-dimensional spatial scene, said electro-optical element having an optically transparent surface including a plurality of pixels, each said pixel having an controllable light transmittance for selectively reducing the intensity of incident light rays propagating from one or more points in said three-dimensional spatial scene, through said pixel, then towards said optical element;
  b) acquiring one or more images of said three-dimensional spatial scene within the field of view of said optical element;
  c) processing said one or more acquired images so as to determine at which pixels the light transmittance is to be actively controlled in order to reduce the intensity of incident light rays by a selected amount before said incident light rays reach said optical element; and
  d) actively controlling the light transmittance of said determined pixels so that after incident light rays propagate through said determined pixels, the incident light rays propagate towards said optical element with an intensity reduced by said selected amount, so that glare produced from points in the three-dimensional spatial scene is automatically reduced.

24. The electro-optical system of claim 23, wherein said control means comprises means for electrically addressing and driving said determined pixels, and wherein the light transmittance of each said pixel is independently controllable.

25. The electro-optical system of claim 23, wherein said electro-optical element comprises an electrically addressable liquid crystal light valve, and wherein the light transmittance of each said pixel is independently controllable.

26. The electro-optical system of claim 23, which further comprises eye-tracking means for determining the position of the eyes of the driver with respect to said electro-optical element, and wherein said image acquisition means is stationarily positionable with respect to said electro-optical element.

27. The electro-optical system of claim 26, wherein said electro-optical element comprises an electrically addressable liquid crystal light valve.

28. The electro-optical system of claim 23, wherein said electro-optical element and said image acquisition means are stationarily positionable with resect to the eyes of the driver.

29. The electro-optical system of claim 28, wherein said electro-optical element comprises an electrically addressable liquid crystal light valve, and wherein the light transmittance of each said pixel is independently controllable.

30. The electro-optical system of claim 23, wherein said electro-optical element comprises first and second electrically addressable liquid crystal light valve panels stationarily positionable with respect to the left and right eyes of the driver.

31. The electro-optical system of claim 30, wherein the light transmittance of each said pixel is independently controllable.

32. The electro-optical system of claim 23, wherein said electro-optical element further comprises a reflective layer adjacent said optically transparent surface so as to reflect incident light rays from behind said optically transparent surface.

33. The electro-optical system of claim 23, which further comprises eye-tracking means for determining the position of the eyes of the driver with respect to said electro-optical element, and wherein said image acquisition means is stationarily positionable with respect to said electro-optical element, and wherein the light transmittance of each said pixel is independently controllable.

34. The electro-optical system of claim 31, wherein said electro-optical elements comprises an electrically addressable liquid crystal light valve.

35. The electro-optical system of claim 23, wherein said image acquisition means comprises a CCD image detecting array.

36. The electro-optical system of claim 26, wherein said eye-tracking means comprises a CCd image detecting array.

37. The electro-optical system of claim 33, wherein said eye-tracking means comprises a CCD image detecting array.

38. An electro-optical system for automatically reducing glare produced from a three-dimensional spatial scene by reducing the intensity of light rays propagating from points in the three-dimensional spatial scene towards the eyes of a driver having a field of view from aboard a vehicle, said electro-optical system comprising:
  an electro-optical element mounted aboard the vehicle and having an optically transparent surface including a plurality of pixels through which the field of view of the eyes of the driver passes, each said pixel having an controllable light transmittance for selectively reducing the intensity of incident light rays propagating from one or more points in the three-dimensional spatial scene, through said pixel, then towards the eyes of the driver;
  image acquisition means for acquiring one or more images of said three-dimensional spatial scene within the field of view of the eyes of the driver;
  image processing means for processing said one or more acquired images and determining at which pixels the light transmittance is to be actively controlled in order to reduce the intensity of incident light rays by a selected amount before reaching the eyes of the driver; and
  control means for actively controlling the light transmittance of said determined pixels so that after incident light rays propagate through said determined pixels, the incident light rays propagate towards the eyes of the driver with an intensity reduced by said selected amount, so that glare produced from the three-dimensional spatial scene is automatically reduced.

39. A method for automatically reducing glare produced from a three-dimensional spatial scene by reducing the intensity of light rays propagating from points in the three-dimensional spatial scene towards the eyes of a driver having a field of view from aboard a vehicle, sad method comprising the steps:
  a) providing an electro-optical element at a desired distance from the eyes of the driver so that the field of view of the driver passes through said electro-optical element, said electro-optical element having an optically transparent surface including a plurality of pixels, each said pixel having a controllable light transmittance for selectively reducing the intensity of incident light rays propagating from one or more points in the three-dimensional spatial scene, through said pixel, then towards the eyes of the driver;
  b) acquiring one or more images of the three-dimensional spatial scene within the field of view of the eyes of the driver;
  c) processing said one or more acquired images so as to determine at which pixels the light transmittance is to be actively controlled in order to reduce the intensity of incident light rays by a selected amount before said incident light rays reach the eyes of the driver; and
  d) actively controlling the light transmittance of said determined pixels so that after incident light rays propagate through said determined pixels, the incident light rays propagate towards the eyes of the driver with an intensity reduced by said selected amount, so that glare produced from the three-dimensional spatial scene is automatically reduced.

40. A method of claim 39, wherein step (d) further comprises independently controlling the light transmittance of each said determined pixel.

41. The method of claim 39, where in step (a) said electro-optical element comprises an electrically addressable liquid crystal light valve, and wherein the light transmittance of each said pixel is independently controlled.

42. The method of claim 41, wherein step (d) further comprises independently controlling the light transmittance of each said determined pixel.

* * * * *